United States Patent
Marat et al.

(10) Patent No.: US 11,401,236 B2
(45) Date of Patent: Aug. 2, 2022

(54) RESORCINOL DERIVATIVES FOR THEIR COSMETIC USE

(71) Applicant: L'OREAL, Paris (FR)

(72) Inventors: Xavier Marat, Aulnay-sous-Bois (FR); Chunyu Ma, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/615,936

(22) PCT Filed: May 30, 2018

(86) PCT No.: PCT/EP2018/064199
§ 371 (c)(1),
(2) Date: Nov. 22, 2019

(87) PCT Pub. No.: WO2018/220020
PCT Pub. Date: Dec. 6, 2018

(65) Prior Publication Data
US 2020/0140376 A1    May 7, 2020

(30) Foreign Application Priority Data

May 31, 2017  (FR) ...................... 1754811

(51) Int. Cl.
| | | |
|---|---|---|
| *C07C 235/34* | (2006.01) | |
| *A61K 8/42* | (2006.01) | |
| *A61K 8/49* | (2006.01) | |
| *A61Q 19/02* | (2006.01) | |
| *C07C 235/36* | (2006.01) | |
| *C07D 265/30* | (2006.01) | |
| *C07D 319/06* | (2006.01) | |

(52) U.S. Cl.
CPC .............. *C07C 235/34* (2013.01); *A61K 8/42* (2013.01); *A61K 8/498* (2013.01); *A61Q 19/02* (2013.01); *C07C 235/36* (2013.01); *C07D 265/30* (2013.01); *C07D 319/06* (2013.01)

(58) Field of Classification Search
None
See application file for complete search history.

(56) References Cited

FOREIGN PATENT DOCUMENTS

| JP | 2007-186445 A | 7/2007 | |
|---|---|---|---|
| JP | JR 2007-523932 A | 8/2007 | |
| WO | WO 2005/085169 A1 | 9/2005 | |
| WO | WO 2014/092166 * | 6/2014 | ........... A61K 31/216 |
| WO | WO 2014/092166 A1 | 6/2014 | |

OTHER PUBLICATIONS

Machine Translation of Hijikuro et al (WO 2014/092166) (Year: 2014).*
Williams et al (Foye's Principles of Medicinal Chemistry, 5th Ed, pp. 59-63, 2002) (Year: 2002).*

* cited by examiner

*Primary Examiner* — Craig D Ricci
(74) *Attorney, Agent, or Firm* — Polsinelli PC

(57) ABSTRACT

The invention relates to resorcinol-derived compounds of formula (I) and also the salts thereof, the solvates thereof and the optical and/or geometrical isomers thereof, including enantiomers and diastereoisomers, the racemic mixtures thereof, alone or as a mixture. The invention also relates to a cosmetic process for depigmenting, lightening and/or bleaching keratin materials, in particular the skin, using these compounds (I).

8 Claims, No Drawings

RESORCINOL DERIVATIVES FOR THEIR COSMETIC USE

CROSS REFERENCE TO RELATED APPLICATIONS

This application is a National Phase filing under 35 U.S.C. § 371 of PCT/EP2018/064199 filed on May 30, 2018; which application in turn claims priority to Application No. 1754811 filed in France on May 31, 2017. The entire contents of each application are hereby incorporated by reference.

The present invention relates to resorcinol-derived compounds of formula (I) and also to the cosmetic use thereof for depigmenting and/or bleaching the skin.

At various periods of their life, some people see the appearance on their skin, and more in particular on the hands and the face, of darker and/or more coloured spots, which give the skin heterogeneity. These blemishes are due in particular to a high concentration of melanin in the keratinocytes situated at the surface of the skin.

The use of inoffensive topical depigmenting substances which are highly effective is very particularly sought after with a view to treating pigment blemishes.

The mechanism of formation of the pigmentation of the skin, that is to say of the formation of melanin, is particularly complex and involves, schematically, the following main stages:

Tyrosine→Dopa→Dopaquinone→Dopachrome→Melanin

Tyrosinase (monophenol dihydroxy phenylalanine: oxygen oxidoreductase EC 1.14.18.1) is the essential enzyme involved in this sequence of reactions. In particular, it catalyses the conversion reaction of tyrosine to give dopa (dihydroxyphenylalanine), by virtue of its hydroxylase activity, and the conversion reaction of dopa to give dopaquinone, by virtue of its oxidase activity. This tyrosinase acts only when it is in the maturation state under the effect of certain biological factors.

A substance is recognized as depigmenting if it acts directly on the vitality of the epidermal melanocytes where melanogenesis takes place and/or if it interferes with one of the stages of the biosynthesis of melanin, either by inhibiting one of the enzymes involved in melanogenesis or by being inserted as structural analog of one of the chemical compounds in the sequence for the synthesis of melanin, which sequence can then be blocked and thus ensure depigmentation.

Certain resorcinol derivatives are already known in the prior art for their depigmenting activity. In this regard mention may in particular be made of documents WO 2005/085169, WO 2004/017936, EP623339 and JP11255638.

Arbutin and kojic acid are in particular known as depigmenting agents for the skin.

Substances have been sought which exhibit an effective depigmenting action, in particular superior to that of arbutin and kojic acid.

There is still a need for a novel agent for bleaching human skin, the action of which is as efficient as the known agents, but which does not have their drawbacks, i.e. which is not irritant, not toxic and/or not allergizing for the skin, while at the same time being stable in a composition, or alternatively which has reinforced action so as to be able to be used in lower amounts, which considerably reduces the side effects observed.

In this regard, the Applicant has discovered, surprisingly and unexpectedly, that certain resorcinol derivatives have good depigmenting activity, even at low concentration.

The subject of the invention is therefore the compounds of formula (I) as defined below, with the exception of the compound (I) for which $R_1=R_2=H$, $R=Me$, and $R_4=OH$.

Likewise, a subject of the invention is a composition comprising, in a physiologically acceptable medium, at least one compound of formula (I) as defined below.

The invention also relates to the non-therapeutic cosmetic use of at least one compound of formula (I) as defined below, or of a composition containing said compound(s), as an agent for bleaching, lightening and/or depigmenting keratin materials, especially the skin.

A subject of the invention is also a non-therapeutic cosmetic treatment process for depigmenting, lightening and/or bleaching keratin materials, especially the skin, comprising the application to the skin of at least one compound of formula (I) as defined below or of a composition containing said compound(s).

A subject of the invention is also the compounds of formula (I) as defined below, or a composition containing said compound (s), for the dermatological use thereof for depigmenting the skin.

The compounds of formula (I), as defined below, make it possible to depigment and/or lighten efficiently, or even bleach, human skin. They are in particular intended to be applied to the skin of individuals bearing brownish pigmentation spots or senescence spots, or to the skin of individuals wishing to combat the appearance of a brownish colour caused by melanogenesis.

For the purposes of the present invention, the term "keratin materials" is intended to mean human keratin materials, and in particular human skin, bodily hair, eyelashes, head hair, lips and nails.

Said compounds may also make it possible to depigment and/or lighten bodily hairs, the eyelashes, head hair, and also the lips and/or the nails.

A subject of the invention is therefore compounds which correspond to formula (I) below, with the exception of the compound (I) for which $R_1=R_2=H$, $R=Me$, and $R_4=OH$:

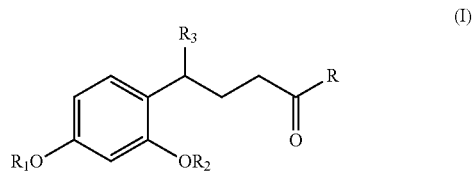

in which:

$R_1$ and $R_2$, which may be identical or different, denote:
a) a hydrogen atom H,
b) a radical $COR_8$ in which $R_8$ denotes a saturated linear $C_1$-$C_{20}$ alkyl radical, an unsaturated linear $C_2$-$C_{20}$ alkyl radical, a branched saturated or unsaturated $C_3$-$C_{20}$ radical or a $C_3$-$C_8$ cycloalkyl radical,
c) a radical S* denoting a monosaccharide sugar radical or a polysaccharide sugar radical comprising from 2 to 5 saccharide units, preferably from 2 to 3 saccharide units, preferentially a sugar radical comprising 1 or 2 saccharide units (monosaccharide or disaccharide), said monosaccharide or polysaccharide radical S* being connected to the rest of the molecule via a bond between the carbon atom C1 of one of the sugars of said monosaccharide or polysaccharide radical, this bond possibly being α or β anomeric, $R_3$ denotes a saturated $C_1$-$C_{20}$ or unsaturated $C_2$-$C_{20}$, linear or branched $C_3$-$C_{20}$ or cyclic $C_3$-$C_8$ alkyl radical, R denotes:
- a radical $OR_5$ in which $R_5$ denotes H or a saturated linear $C_1$-$C_{20}$ alkyl radical, an unsaturated linear $C_2$-$C_{20}$ alkyl radical, a saturated or unsaturated, branched $C_3$-$C_{20}$ alkyl radical or a $C_3$-$C_8$ cycloalkyl radical, said alkyl radical being optionally substituted with one or more hydroxyl radicals and/or with one or more heterocycles and/or said alkyl radical being optionally interrupted with one or more non-adjacent heteroatoms or groups, in particular one to three, chosen from N, O, —CO— or combinations thereof, such as —NHCO—,
- a radical $NR_6R_7$ in which $R_6$ and $R_7$ independently denote:
  - a) a hydrogen atom H,
  - b) a saturated $C_1$-$C_{20}$ or unsaturated $C_2$-$C_{20}$ or branched $C_3$-$C_{20}$ or cyclic $C_3$-$C_8$ alkyl radical, optionally interrupted with one or more non-adjacent heteroatoms or groups, especially one to three, chosen from N, O, —CO— and combinations thereof such as —NHCO—, —NHCONH—, and/or optionally substituted with one or more identical or different groups, especially one to three, chosen from:
    - i) —$OR_9$
    - ii) —$SR_9$
    - iii) —$NR_9R_{10}$
    - iv) —$CONR_9R_{10}$
    - v) —$COOR_9$
    - vi) —$NHCONHR_9$
    - vii) —$C(O)alkyl(C_1$-$C_4)$
    - viii) a saturated or unsaturated non-aromatic (hetero)cyclic group, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group
    - ix) a $C_5$-$C_{12}$ (hetero)aryl group optionally substituted with one or more hydroxyl radicals, especially one to three, and/or with one or more $C_1$-$C_8$ alkoxy and/or $C_1$-$C_8$ alkyl radicals, in particular one to three
    - x) —NH—C=NH(NH$_2$) (guanidine group)

$R_9$ and $R_{10}$, which may be identical or different, being chosen from H, a saturated linear $C_1$-$C_{10}$ alkyl group, an unsaturated linear $C_2$-$C_{10}$ alkyl group, a saturated or unsaturated branched $C_3$-$C_{10}$ alkyl group, and a $C_3$-$C_8$ cycloalkyl group; a $(C_1$-$C_4)alkyl(C_6)(hetero)aryl$ group optionally containing a nitrogen atom, especially a benzyl group; an acetyl radical;

$R_9$ and $R_{10}$ possibly forming with the nitrogen that bears them a 5- to 8-membered heterocycle, which may contain one or more heteroatoms or groups chosen from N, O, —CO—, especially one to three, and/or optionally substituted with a $C_1$-$C_{10}$ hydrocarbon-based chain, in particular alkyl;

c) a radical $NR_{11}R_{12}$ with $R_{11}$ and $R_{12}$ independently denoting a radical chosen from:
- i) —H
- ii) a saturated linear $C_1$-$C_{10}$ or unsaturated $C_2$-$C_{10}$ or branched $C_3$-$C_{10}$ or cyclic $C_3$-$C_8$ alkyl group, optionally interrupted with one or more heteroatoms or groups chosen from N, O, —CO and combinations thereof such as —NHCO—, —NHCONH—, and/or optionally substituted with one or more identical or different $C_1$-$C_8$ alkyl groups, especially one to three
- iii) a $C_5$-$C_{12}$ (hetero)aryl group, optionally containing one or more heteroatoms chosen from O, N and S, especially one to three, optionally substituted with one or more hydroxyls and/or with one or more $C_1$-$C_8$ alkoxy radicals, especially one to three; $R_{11}$ and $R_{12}$ possibly forming with the nitrogen that bears them a 5- to 8-membered heterocycle, which may contain one or more heteroatoms or groups chosen from N, O and —CO—, especially one to three, and/or optionally substituted with a $C_1$-$C_{10}$ hydrocarbon-based chain optionally containing one or more radicals chosen from hydroxyl and $C_1$-$C_4$ alkoxy, especially one to three;

d) a radical $OR_{13}$ with $R_{13}$ denoting a radical chosen from:
- i) —H
- ii) a saturated linear $C_1$-$C_{10}$ or branched $C_3$-$C_{10}$ or cyclic $C_3$-$C_8$ alkyl group, $R_6$ and $R_7$ possibly forming with the nitrogen that bears them a 5- to 8-membered heterocycle, which may contain one or more heteroatoms or groups chosen from N, O, —CO—, especially one to three, and/or optionally substituted with a $C_1$-$C_{10}$ hydrocarbon-based chain;

and also the salts thereof, the solvates thereof and the optical and/or geometrical isomers thereof, including enantiomers and diastereoisomers, and the racemic mixtures thereof, alone or as a mixture.

In the context of the present invention, it is understood that:
when the radical S* represents a monosaccharide radical, it may be in pyranose form (the sugar heterocycle which forms it is 6-membered) or furanose form (the sugar heterocycle which forms it is 5-membered); and
when said radical S* represents a polysaccharide radical, it comprises the sequence of 2 to 5 identical or different saccharide units which may be in furanose or pyranose form.

These definitions of the radical S* apply to the compounds of formula (I) as defined previously.

Preferably, the polysaccharide is a disaccharide which results from the sequence of a saccharide unit in furanose form and a unit in pyranose form or the sequence of a saccharide unit in pyranose form and a unit in furanose form; whether it is for the monosaccharide or polysaccharide radical, each saccharide unit may be in levorotatory L or dextrorotatory D form, and α or β anomeric form.

Preferably, the monosaccharide is chosen from glucose, galactose, mannose, xylose, lyxose, fucose, arabinose, rhamnose, quinovose, fructose, sorbose, talose, N-acetylglucosamine and N-acetylgalactosamine, and preferably glucose, galactose, mannose, xylose, lyxose, fucose, arabinose, rhamnose and fructose.

According to another embodiment, the polysaccharide radical may be formed from 2 to 5 saccharide units, in particular from 2 to 3 and preferably 2 saccharide units, linked together via a 1→4 (C1 of one saccharide unit→C4 of the other saccharide unit) or 1→3 (C1 of one saccharide unit→C3 of the other saccharide unit) or 1→6 (C1 of one saccharide unit→C6 of the other saccharide unit) oxygen atom (oxy) 5, each saccharide unit of which is formed from a heterocycle comprising 4 or 5 carbon atoms.

When the polysaccharide radical is a disaccharide, it may be chosen from: lactose, maltulose, palatinose, lactulose, amygdalose, turanose, cellobiose, isomaltose, rutinose and maltose; and preferably it may be maltose.

Still within the context of the present invention, the salts of the compounds of formula (I) as defined below comprise the conventional non-toxic salts of said compounds such as those formed from acid or base.

As salts of the compound of formula (I) (when it comprises a quaternizable nitrogen atom), mention may be made of:

a) the salts obtained by addition of the compound of formula (I) to a mineral acid, chosen especially from hydrochloric, boric, hydrobromic, hydriodic, sulfuric, nitric, carbonic, phosphoric and tetrafluoroboric acids;

b) or the salts obtained by addition of the compound of formula (I) to an organic acid, chosen especially from acetic, propionic, succinic, fumaric, lactic, glycolic, citric, gluconic, salicylic, tartaric, terephthalic, methanesulfonic, ethanesulfonic, benzenesulfonic, toluenesulfonic and triflic acids.

Mention may also be made of the salts obtained by addition of the compound of formula (I) (when it comprises an acid group) to a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate, for example;

or to an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino)propylamine.

Mention may also be made of the salts of amino acids, for instance lysine, arginine, guanidine, glutamic acid and aspartic acid. Advantageously, the salts of the compounds of formula (I) (when it comprises an acid group) may be chosen from alkali metal or alkaline-earth metal salts such as sodium, potassium, calcium or magnesium salts; ammonium salts.

Advantageously, the salts of the compounds of formula (I) (when it comprises a quaternizable nitrogen atom) may be chosen from halides such as chloride or bromide; citrate, acetate, succinate, phosphate, lactate, tartrate.

The acceptable solvates of the compounds described in the present invention comprise conventional solvates such as those formed during the preparation of said compounds owing to the presence of solvents. Examples that may be mentioned include solvates due to the presence of water or of linear or branched alcohols, such as ethanol or isopropanol.

The optical isomers are in particular the enantiomers and the diastereoisomers.

Still in the context of the present invention:

A "$(C_x\text{-}C_y)$alkyl group" denotes an alkyl group comprising from x to y carbon atoms. Such an alkyl group may be linear and saturated and typically contain from 1 to 20 carbon atoms or else from 1 to 10 carbon atoms, or even 1 to 4 carbon atoms. It may also be linear and unsaturated and typically contain from 2 to 20 carbon atoms or from 2 to 10 carbon atoms. It may also be branched and typically contain from 3 to 20 carbon atoms or from 3 to 10 carbon atoms. The names $(C_x\text{-}C_y)$alkyl or $C_x\text{-}C_y$ alkyl are equivalent. An alkyl group may also be cyclic: it is then a cycloalkyl group which may typically contain from 3 to 8 carbon atoms.

Unless otherwise indicated, a "$(C_x\text{-}C_y)$alkyl group" denotes a saturated linear alkyl group comprising from x to y carbon atoms.

Preferentially, the linear saturated or branched alkyl groups may be chosen from: methyl, ethyl, propyl, isopropyl, butyl, isobutyl, tert-butyl, pentyl, hexyl, heptyl, 2-ethylhexyl, octyl, nonyl, decyl, undecyl, dodecyl, tridecyl, tetradecyl, pentadecyl, hexadecyl, heptadecyl, octadecyl, nonadecyl and eicosyl.

More preferentially, the linear saturated or branched alkyl groups may be chosen from: methyl, ethyl, propyl, isopropyl, butyl, isobutyl, tert-butyl, pentyl, hexyl, heptyl, 2-ethylhexyl and octyl.

The cycloalkyl group may be chosen from: cyclopropyl, cyclobutyl, cyclopentyl, cyclohexyl, cycloheptyl and cyclooctyl, in particular cyclohexyl.

A "$(C_x\text{-}C_y)$alkoxy group" denotes a linear and, where appropriate, branched group of formula $-O(C_x\text{-}C_y)$ alkyl which may typically contain from 1 to 8 carbon atoms or from 1 to 4 carbon atoms.

The alkoxy group may be chosen from methoxy, ethoxy, propoxy and butoxy and may more particularly be a methoxy group;

A "saturated or unsaturated non-aromatic (hetero)cyclic group" denotes a monocyclic or bicyclic carbocyclic group having from 5 to 12 ring members, in particular from 5 to 8 ring members, and possibly containing one to three heteroatoms or groups chosen from N, O, S and —C(O)—, preferably N and/or O. A heterocyclic group denotes a monocyclic or bicyclic carbocyclic group having from 5 to 12 ring members, in particular from 5 to 8 ring members, and containing one to three heteroatoms or groups chosen from N, O, S and —C(O)—, preferably N and/or O.

Such a (hetero)cyclic group may be chosen from cyclohexyl, piperidyl, morpholinyl, piperazinyl, imidazolyl and pyrrolidinyl. Preferentially, it is a cyclohexyl or morpholinyl ring.

A "(hetero)aryl group" denotes a monocyclic or bicyclic carbocyclic group containing from 5 to 12 carbon atoms and possibly containing one to three heteroatoms chosen from N, O and S, and in which at least one of the rings is aromatic. An "aryl group" denotes a monocyclic or bicyclic carbocyclic group containing from 5 to 12 carbon atoms, in which at least one of the rings is aromatic. A "heteroaryl group" denotes a monocyclic or bicyclic carbocyclic group containing from 5 to 12 carbon atoms and containing one to three heteroatoms chosen from N, O and S, and in which at least one of the rings is aromatic.

The (hetero)aryl radicals may be chosen from phenyl, naphthyl, indenyl, fluorenyl and anthracenyl. Preferentially, the (hetero)aryl radicals denote aryl radicals and they are in particular the phenyl group.

The heteroaryl radicals may be chosen from furyl, acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof.

It is understood in the context of the present invention that when a first radical is substituted with one or more second radicals, the term "more" may mean two or three.

Similarly, when a first cyclic radical optionally contains one or more heteroatoms or groups, the term "more" may mean two or three.

According to one particular form of the invention, the compounds of formula (I) and also the salts, solvates and/or isomers thereof are such that $R_1$ and $R_2$ independently denote:
  a) H,
  b) a radical $COR_8$ in which $R_8$ denotes a saturated linear $C_1$-$C_{20}$ alkyl radical, an unsaturated linear $C_2$-$C_{20}$ alkyl radical, a branched saturated or unsaturated $C_3$-$C_{20}$ radical or a $C_3$-$C_8$ cycloalkyl radical, and preferably a saturated $C_1$-$C_4$ alkyl, such as a methyl radical.

According to another particular form of the invention, $R_3$ denotes a saturated $C_1$-$C_{20}$ or unsaturated $C_2$-$C_{20}$ alkyl radical which is linear or branched $C_3$-$C_{20}$ or cyclic $C_3$-$C_8$; more preferentially, $R_3$ denotes a saturated $C_1$-$C_{10}$ or unsaturated $C_2$-$C_{10}$, alkyl radical, and even more preferentially $R_3$ denotes a saturated $C_1$-$C_4$ alkyl radical, such as methyl.

According to one particular variant of the invention, the compounds of formula (I) and also the salts, solvates and/or isomers thereof are such that R denotes a radical —$NR_6R_7$ and $R_6$ and $R_7$ form, with the nitrogen atom which bears them, a heterocycle having from 5 to 8 ring members, possibly containing one or more heteroatoms or groups chosen from N, O and —CO—, in particular one to three, and/or optionally substituted with a $C_1$-$C_{10}$ hydrocarbon-based chain, the radicals $R_1$, $R_2$ and $R_3$ having the definitions given previously.

According to this variant, $R_6$ and $R_7$ preferably form, with the nitrogen atom which bears them, a heterocycle having from 5 to 8 ring members, preferably 5 or 6 ring members, or preferentially 6 ring members, said heterocycle possibly containing one or more heteroatoms or groups chosen from N, O and —CO—, in particular one to three, more particularly one heteroatom, and/or said heterocycle being optionally substituted with a $C_1$-$C_{10}$ hydrocarbon-based chain.

According to one preferred form of this variant of the invention, R denotes a radical —$NR_6R_7$ and $R_6$ and $R_7$ form, with the nitrogen atom which bears them, a 6-membered heterocycle containing an oxygen atom; in particular $R_6$ and $R_7$ form, with the nitrogen atom which bears them, a morpholine ring.

By way of example of a compound of formula (1) according to this variant, mention may be made of the compound 29 subsequently described and also the salts, solvates and/or isomers thereof.

According to another variant of the invention, the compounds of formula (I) and also the salts, solvates and/or isomers thereof are such that R denotes a radical —$NR_6R_7$ in which $R_6$ and $R_7$ independently denote:
  a) H,
  b) a saturated $C_1$-$C_{20}$ or unsaturated $C_2$-$C_{20}$ or branched $C_3$-$C_{20}$ or cyclic $C_3$-$C_8$ alkyl radical, optionally interrupted with one or more non-adjacent heteroatoms or groups, especially one to three, chosen from N, O, —CO— and combinations thereof such as —NHCO—, —NHCONH—, and/or optionally substituted with one or more identical or different groups, especially one to three, chosen from:
    i) —$OR_9$
    vi) —$COOR_9$
    ix) a saturated or unsaturated non-aromatic (hetero)cyclic group, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group,
    x) a $C_5$-$C_{12}$ (hetero)aryl group optionally substituted with one or more hydroxyl radicals, especially one to three, and/or with one or more $C_1$-$C_8$ alkoxy and/or $C_1$-$C_8$ alkyl radicals, especially one to three,
$R_9$ denoting a) a hydrogen atom or b) a saturated linear $C_1$-$C_{10}$ alkyl group, an unsaturated linear $C_2$-$C_{10}$ alkyl group, a saturated or unsaturated, branched $C_3$-$C_{10}$ alkyl group, or a $C_3$-$C_8$ cycloalkyl group, the radicals $R_1$, $R_2$ and $R_3$ having the definitions defined previously.

By way of examples of compounds of formula (I) according to this variant, mention may be made of the compounds 2, 3, 4, 5, 6, 7, 8, 9, 10, 11, 12, 13, 14, 15, 16, 17, 18, 19, 20, 21, 22, 23, 24, 25, 26, 27, 28 and also the salts, solvates and/or isomers thereof, and more particularly the compounds 2, 3, 4, 5, 6, 7, 8, 9, 10, 11, 14, 15, 17, 18, 20, 22, 24, 25, 26, 27, 28 subsequently described.

According to this variant, $R_6$ and $R_7$ preferably independently denote:
  a) H,
  b) a saturated $C_1$-$C_{10}$ or unsaturated $C_2$-$C_{10}$ or branched $C_3$-$C_{10}$ or cyclic $C_4$-$C_8$ alkyl radical, optionally interrupted with one or more non-adjacent heteroatoms or groups, especially one to three, chosen from N, O, —CO— and combinations thereof such as —NHCO—, —NHCONH—, and/or optionally substituted with one or more identical or different groups, especially one to three, chosen from:
    i) —$OR_9$
    vi) —$COOR_9$
    ix) a saturated or unsaturated non-aromatic (hetero)cyclic group, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group,
    x) a $C_5$-$C_{12}$ (hetero)aryl group optionally substituted with one or more hydroxyl radicals, especially one to three, and/or with one or more $C_1$-$C_8$ alkoxy and/or $C_1$-$C_8$ alkyl radicals, especially one to three,
$R_9$ denoting a) a hydrogen atom or b) a saturated linear $C_1$-$C_{10}$ alkyl group, an unsaturated linear $C_2$-$C_{10}$ alkyl group, a saturated or unsaturated, branched $C_3$-$C_{10}$ alkyl group, or a $C_3$-$C_8$ cycloalkyl group.

According to a first form of this variant, R denotes a radical —$NR_6R_7$ and $R_6$ and $R_7$ are identical and denote a hydrogen atom. By way of example of compounds of formula (I) according to this form of this variant, mention may be made of the compound 10 subsequently described and also the salts, solvates and/or isomers thereof.

According to a second form of this variant, R denotes a radical —$NR_6R_7$ in which $R_6$ denotes a hydrogen atom and $R_7$ is as defined previously. Preferably, R denotes a radical —$NR_6R_7$, $R_6$ denotes a hydrogen atom and $R_7$ denotes:
  $b_1$) a saturated linear or branched $C_1$-$C_{10}$, preferably $C_1$-$C_6$, alkyl radical, said alkyl radical being:
    i1) optionally interrupted with one or more non-adjacent heteroatoms or groups, in particular one to three, chosen from N, O and —CO— or combinations thereof such as —NHCO—, —NHCONH—, said alkyl radical preferably being uninterrupted, and/or
    ii1) optionally substituted with one or more identical or different groups, in particular one to three, chosen from:
      i) —$OR_9$ such as a hydroxyl or methoxy radical
      vi) —$COOR_9$ such as a carboxy radical (COOH) or a $CO_2Et$ radical
      ix) a saturated or unsaturated non-aromatic (hetero)cyclic group, such as a cyclohexyl radical, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group, x) a $C_5$-$C_{12}$ (hetero)aryl group such as a phenyl radical, optionally substituted with one or more hydroxyl radicals, especially one to three, and/or with one or more $C_1$-$C_8$ alkoxy and/or $C_1$-$C_8$ alkyl radicals, especially one to three, said (hetero)aryl radical preferably denoting an aryl radical and more preferentially a phenyl radical or a hydroxyphenyl radical, b$_2$) a cyclic $C_4$-$C_8$, preferably $C_5$-$C_6$, alkyl radical and more preferentially a cyclohexyl radical, said cyclic alkyl radical being optionally substituted with one or more identical or different groups, in particular one to three, chosen from:

i) —$OR_9$
vi) —$COOR_9$
ix) a saturated or unsaturated non-aromatic (hetero)cyclic group, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group,
x) a $C_5$-$C_{12}$ (hetero)aryl group optionally substituted with one or more hydroxyl radicals, especially one to three, and/or with one or more $C_1$-$C_8$ alkoxy and/or $C_1$-$C_8$ alkyl radicals, especially one to three, said cyclic alkyl radical preferably being unsubstituted, $R_9$ denoting a) a hydrogen atom or b) a saturated linear $C_1$-$C_{10}$ alkyl group, an unsaturated linear $C_2$-$C_{10}$ alkyl group, a saturated or unsaturated, branched $C_3$-$C_{10}$ alkyl group, or a $C_3$-$C_8$ cycloalkyl group, and $R_9$ preferably denoting a hydrogen atom or a $C_1$-$C_4$ alkyl radical.

By way of examples of compounds of formula (I) according to this form of this variant, mention may be made of the compounds 2, 3, 4, 5, 6, 7, 8, 9, 11, 12, 13, 14, 15, 16, 17, 18, 19, 20, 21, 22, 23 and also the salts, solvates and/or isomers thereof, and more particularly the compounds 2, 3, 4, 5, 6, 7, 8, 9, 11, 14, 15, 17, 18, 20, 22 subsequently described.

According to a third form of this variant, $R_6$ and $R_7$ preferably independently denote an alkyl radical which is saturated $C_1$-$C_{10}$ or unsaturated $C_2$-$C_{10}$ or branched $C_3$-$C_{10}$ or cyclic $C_4$-$C_8$, preferably a saturated linear $C_1$-$C_{10}$ alkyl radical and more preferentially a saturated linear $C_1$-$C_4$ alkyl radical, said alkyl radical being:

i) optionally interrupted with one or more non-adjacent heteroatoms or groups, in particular one to three, chosen from N, O and —CO— or combinations thereof such as —NHCO—, —NHCONH—, preferably uninterrupted, and/or ii) optionally substituted with one more or identical or different groups, in particular one to three, chosen from:
  i) —$OR_9$ such as hydroxyl or methoxy,
  vi) —$COOR_9$ such as COOH or COOEt,
  ix) a saturated or unsaturated non-aromatic (hetero)cyclic group, said (hetero)cyclic group being optionally substituted with one or more hydroxyls, especially one to three, and/or with one or more $C_1$-$C_8$ alkoxy and/or $C_1$-$C_8$ alkyl radicals, especially one to three; one of the chain members of the (hetero)cyclic group possibly being a carbonyl group,
  x) a $C_5$-$C_{12}$ (hetero)aryl group optionally substituted with one or more hydroxyl radicals, especially one to three, and/or with one or more $C_1$-$C_8$ alkoxy and/or $C_1$-$C_8$ alkyl radicals, especially one to three, $R_9$ denoting a) a hydrogen atom or b) a saturated linear $C_1$-$C_{10}$ alkyl group, an unsaturated linear $C_2$-$C_{10}$ alkyl group, a saturated or unsaturated, branched $C_3$-$C_{10}$ alkyl group, or a $C_3$-$C_8$ cycloalkyl group, and $R_9$ preferably denoting a hydrogen atom or a $C_1$-$C_4$ alkyl radical.

Preferably, according to this third form of this variant, $R_6$ and $R_7$ independently denote a saturated $C_1$-$C_{10}$, preferably saturated $C_1$-$C_4$, alkyl radical, said alkyl radical being optionally substituted with one to three identical or different groups, in particular one, chosen from: hydroxyl, $C_1$-$C_4$ alkoxy such as methoxy, carboxy (COOH), $C_1$-$C_4$ alkoxycarbonyl, such as COOEt.

By way of examples of compounds of formula (I) according to this form of this variant, mention may be made of the compounds 24, 25, 26, 27 and 28 and also the salts, solvates and/or isomers thereof, subsequently described.

According to another variant of the invention, the compounds of formula (I) and also the salts, solvates and/or isomers thereof are such that R denotes a radical —$OR_5$ in which $R_5$ denotes H or a saturated linear $C_1$-$C_{20}$ alkyl radical or an unsaturated linear $C_2$-$C_{20}$ alkyl radical or a saturated or unsaturated, branched $C_3$-$C_{20}$ alkyl radical or a $C_3$-$C_8$ cycloalkyl radical, said alkyl radical being optionally interrupted with one or more hydroxyl radicals and/or with one or more heterocycles and/or said alkyl radical being optionally interrupted with one or more non-adjacent heteroatoms or groups, in particular one to three, chosen from N, O and —CO— or combinations thereof such as —NHCO—, the radicals $R_1$, $R_2$ and $R_3$ having the definitions given previously.

By way of examples of compounds of formula (I) according to this variant, mention may be made of the compounds 1, 30, 31, 32 and 34 and also the salts, solvates and/or isomers thereof, and more particularly the compounds 1, 30, 32 and 34, subsequently described. Preferably, according to this variant, $R_5$ denotes a saturated linear $C_1$-$C_{15}$ alkyl radical, an unsaturated linear $C_2$-$C_{20}$ alkyl radical, or a saturated or unsaturated, branched $C_3$-$C_{20}$ alkyl radical, said alkyl radical being optionally substituted with one or more hydroxyl radicals and/or with one or more heterocycles and/or said alkyl radical being optionally interrupted with one or more non-adjacent heteroatoms or groups, in particular one to three and preferably one, chosen from N, O and —CO— or combinations thereof such as —NHCO—, preferably —NH—CO—, the radicals $R_1$, $R_2$ and $R_3$ having the definitions given previously, and in particular the compounds of formula (I) denote the compounds 30, 31, 32 and 34 and also the salts, solvates and/or isomers thereof, and even more particularly the compounds 30, 32 and 34, subsequently described.

The various schemes below describe the various synthetic routes for obtaining the compounds of formula (I). In these schemes, "a.t." means ambient temperature.

The compounds (I) of the invention may be prepared according to scheme 1 below.

Scheme 1

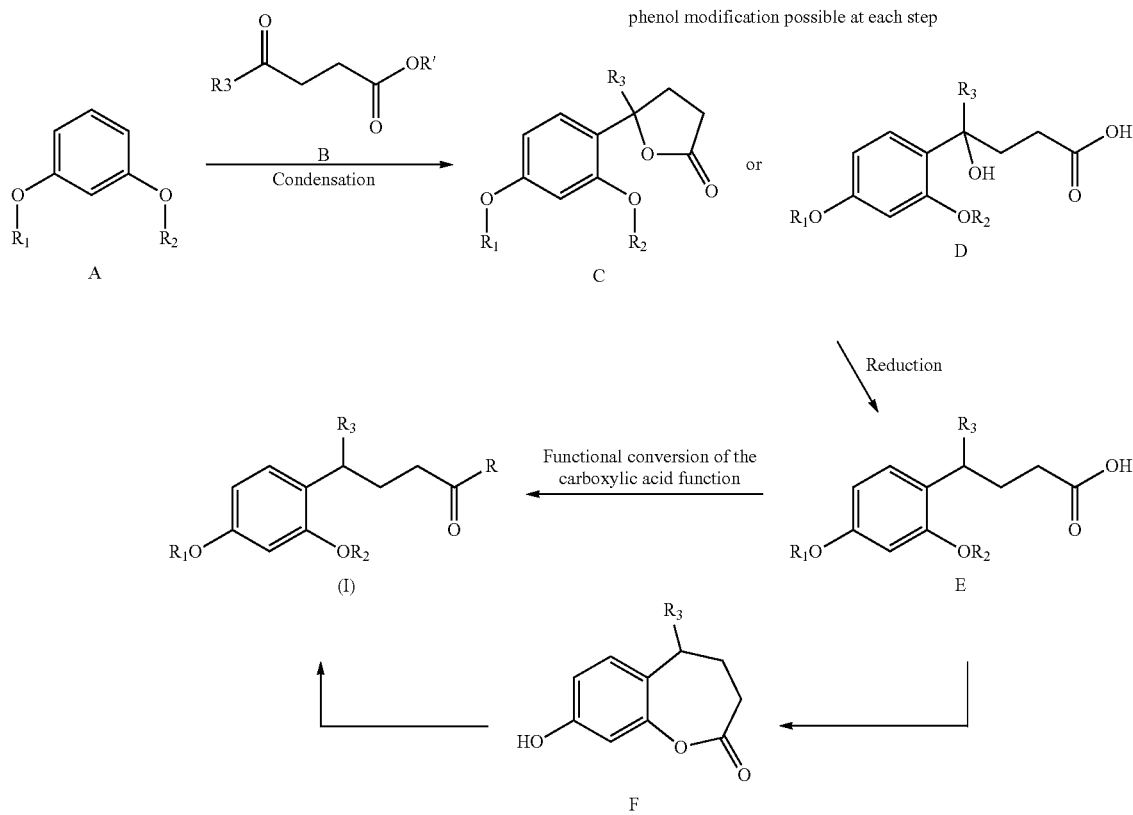

According to this scheme 1, the synthesis of the compounds (I) involves the key intermediate of lactone C type (or its open gamma-hydroxy acid form D), the synthesis of which is described in the publications by R Gopal; P Gupta Synthesis of succin-as-eins; Bulletin of the Chemical Society of Japan, 47, 7, 1789-1790 and 48, 7, 2227-2228 and 49, 7, 2027-2028. Those skilled in the art can adapt the strategy therefrom as a function of the $R_3$ groups desired.

The resorcinol A can react in the presence of a gamma-keto ester B (R'=H or saturated $C_1$-$C_6$ alkyl) to give the lactone C or its open form D. These lactones can be reduced by catalytic hydrogenation under the conditions known to those skilled in the art to give E.

The acid function of E can then be converted in the presence of amine $NHR_6R_7$ and of an activating agent or in the presence of alcohol $R_5OH$ optionally with beforehand any modifications of the phenolic functions (if R1 and/or R2=H) by strategies known to those skilled in the art in terms of reaction and protection/deprotection (formation of esters, of ethers or glycosylations).

Production of the derivatives C and D via reaction between A and B may be performed in particular in the presence of water or of an organic solvent that may be chosen from toluene, tetrahydrofuran, heptane, isooctane, methyltetrahydrofuran, methyl ethyl ketone, methyl isobutyl ketone, dioxane, ethyl acetate, isopropyl acetate and isododecane, and mixtures thereof, especially at a temperature of between 15 and 200° C., optionally in the presence of a catalyst (acidic) as described in the publications: Synthesis of 7-hydroxycoumarins by Pechmann reaction using Nafion resin/silica nanocomposites as catalysts: Laufer M C, Hausmann H, Hölderich W F, *J of Catalysis,* 2003, 218, 315-320; Synthesis of 7-hydroxycoumarins catalysed by solid acid catalysts: Hoefnagel A, Gunnewegh E, Downing R, van Bekkum H, *J Chem Soc Chem Commun,* 1995, 225-226; in particular in the presence of an acid catalyst such as sulfuric acid, methanesulfonic acid, triflic acid or para-toluenesulfonic acid, sulfonic resins such as Dowex® or Amberlyst® resins (sold by Aldrich).

The compounds of formula (I) for which $R_1$ and/or $R_2$ denote a group $COR_8$ may be obtained by acetylation/esterification. The acetylation/esterification reaction may be performed with the anhydride $R_8COOCOR_8$ (such as acetic anhydride) or acetyl chloride $R_8COCl$ (or such as acetyl chloride), in particular in the presence of an aprotic solvent such as toluene, pyridine or tetrahydrofuran. The acetylation reaction may be selective by employing protecting groups on the functions that do not need to be acetylated and by performing a deprotection reaction after acetylation, according to the known techniques of organic synthesis.

In addition, when the final compounds (I) are such that the radicals $R_6$ and/or $R_7$ contain a free carboxylic acid, said compounds can be obtained by saponification using mineral bases, for instance NaOH or LiOH in the presence of protic or aprotic solvents, for instance ethanol or tetrahydrofuran or water at temperatures ranging between 0 and 100° C. The salts obtained can then be reacidified in the presence of standard mineral or organic acids, for instance: hydrochloric acid, citric acid.

All of these steps may also make use of protection/deprotection strategies usually used in organic chemistry and compiled in the book Protecting Groups in Organic Synthesis, Greene, Wuts, Wiley Interscience, depending on the nature of the radicals.

The compounds of formula (I) for which $R_1=R_2=H$ (or $COR_8$) and $R_3=CH_3$, R being as defined previously, can also be obtained according to scheme 2 below. Thus, the present application also relates to a process for preparing a compound of formula (I) as defined previously, which consists in (i) reacting a compound of formula E, in which $R_3$ is as defined previously, by activating the carboxylic acid function with a view to forming a 7-membered lactone (F), then

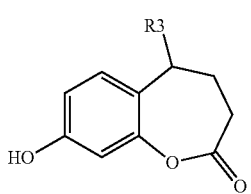

(F)

(ii) reacting the compound obtained in step (i) with a compound of formula $HNR_6R_7$, in the presence of an organic solvent, especially tetrahydrofuran, dioxane, dimethylformamide, dimethyl sulfoxide, 2-methyltetrahydrofuran, dichloromethane; toluene, methanol or ethanol; optionally in the presence of a catalyst chosen from Lewis or Brønsted acid catalysts and basic catalysts, such as potassium carbonate, triethylamine or diisopropylethylamine; optionally by heating to a temperature of between 15° C. and 200° C., especially between 20° C. and 150° C., so as to obtain the compound of formula (G) below

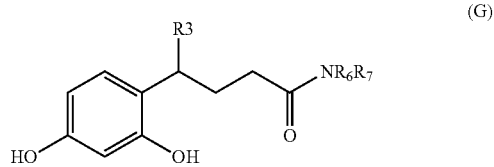

(G)

in which $R_3$, $R_6$ and $R_7$ are as defined above, said compound of formula (G) being able to subsequently give rise to a modification of the hydroxyl groups in order to obtain derivatives of formula (I) for which $R_1$ and/or $R_2$ are different from a hydrogen atom.

Scheme 2

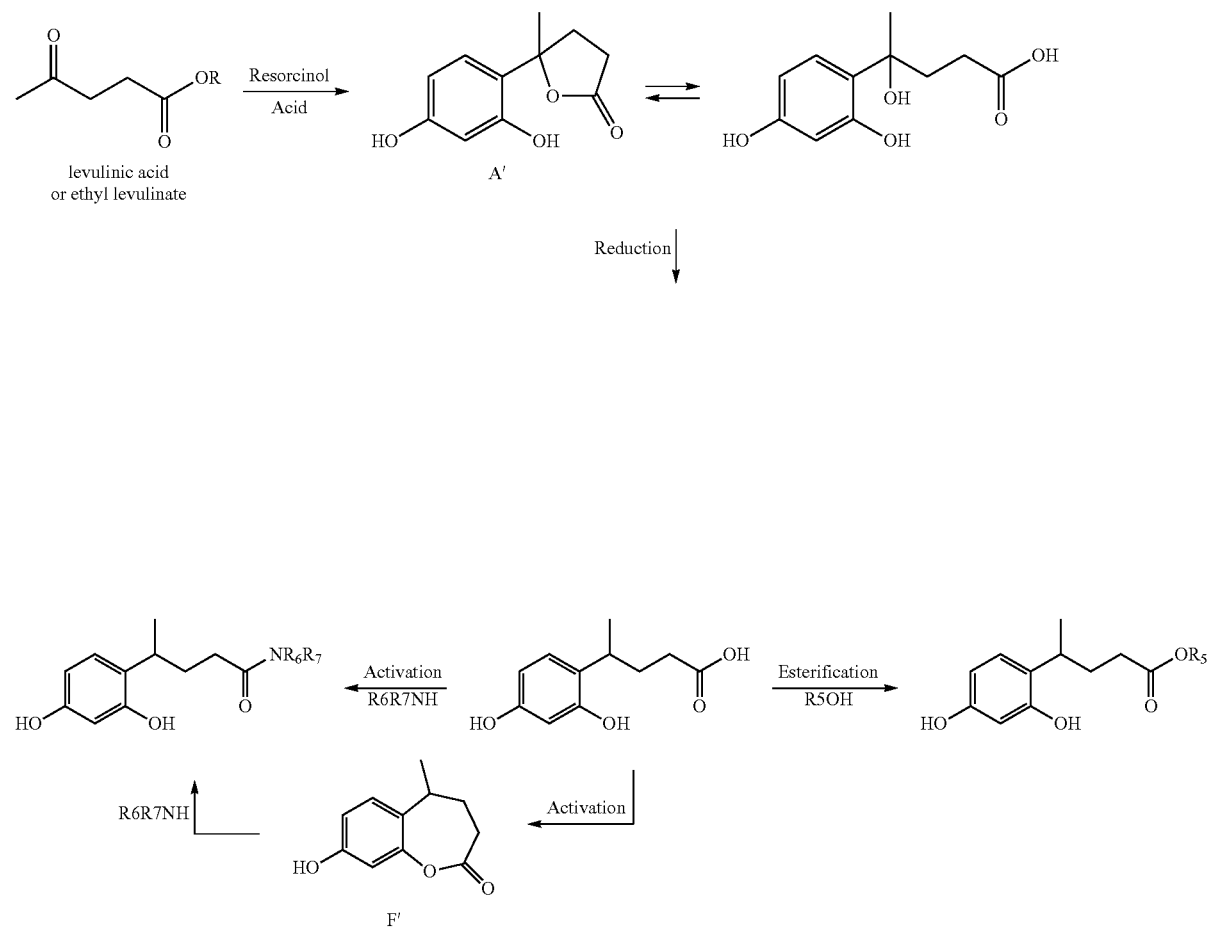

According to this scheme 2, the compound of formula (I) such that $R_1=R_2=H$ and $R_3=CH_3$ and R is as defined above, can be obtained via a succession of three to five steps. With reference to the literature, R Gopal; P Gupta Synthesis of succin-as-eins; Bulletin of the Chemical Society of Japan, 47, 7, 1789-1790 and 48, 7, 2227-2228, an adapted procedure was used to obtain the compound A' with concentrated sulfuric acid and also a solvent and a catalyst. A' can easily be modified using the methods known to those skilled in the art (described in Comprehensive Organic Transformations, A Guide to Functional Group Preparations, Two Volume Set, 2nd Edition, Richard C. Larock, ISBN: 978-1-118-03758-4) such as amidation, esterification or cyclization via the formation of the heptacyclic lactone (F'). This lactone can then be opened with primary or secondary amines so as to obtain the compounds of formula (I) in which $R_1=R_2=H$ and $R_3=CH_3$ and $R_5$ and $R_6$ and $R_7$ have the definitions reported above.

Examples of compounds of formula (I) of the invention are collated in Table 1 below.

TABLE 1

The numbers in the table correspond to the numbers used in the examples below.

| Compound No. | Structure | Chemical name |
|---|---|---|
| 1 | 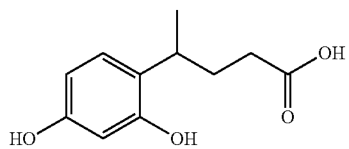 | 4-(2,4-dihydroxyphenyl)pentanoic acid |
| 2 | 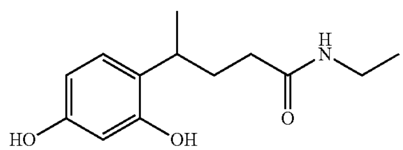 [SMILES: CCNC(=O)CCC(C)c1ccc(O)cc1O] | 4-(2,4-dihydroxyphenyl)-N-ethylpentanamide |
| 3 | 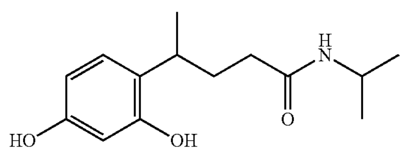 [SMILES: CC(C)NC(=O)CCC(C)c1ccc(O)cc1O] | 4-(2,4-dihydroxyphenyl)-N-(propan-2-yl)pentanamide |
| 4 | 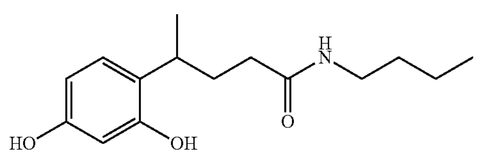 [SMILES: CCCCNC(=O)CCC(C)c1ccc(O)cc1O] | N-butyl-4-(2,4-dihydroxyphenyl)pentanamide |
| 5 | 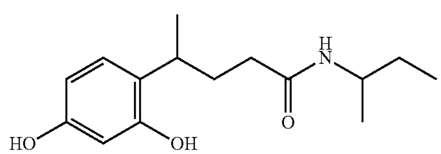 [SMILES: CCC(C)NC(=O)CCC(C)c1ccc(O)cc1O] | N-(butan-2-yl)-4-(2,4-dihydroxyphenyl)pentanamide |
| 6 | 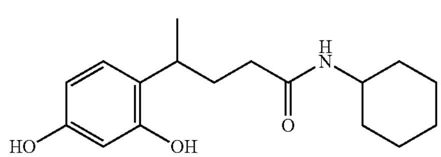 [SMILES: CC(CCC(=O)NC1CCCCC1)c1ccc(O)cc1O] | N-cyclohexyl-4-(2,4-dihydroxyphenyl)pentanamide |
| 7 | 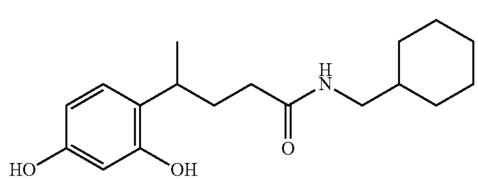 [SMILES: CC(CCC(=O)NCC1CCCCC1)c1ccc(O)cc1O] | N-(cyclohexylmethyl)-4-(2,4-dihydroxyphenyl)pentanamide |

TABLE 1-continued

The numbers in the table correspond to the numbers used in the examples below.

| Compound No. | Structure | Chemical name |
|---|---|---|
| 8 | 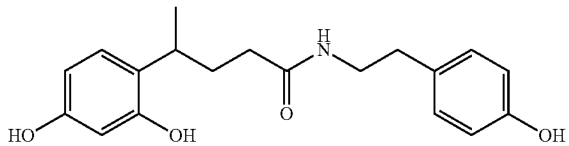 [SMILES: CC(CCC(=O)NCCc1ccc(O)cc1)c1ccc(O)cc1O] | 4-(2,4-dihydroxyphenyl)-N-[2-(4-hydroxyphenyl)ethyl]pentanamide |
| 9 | 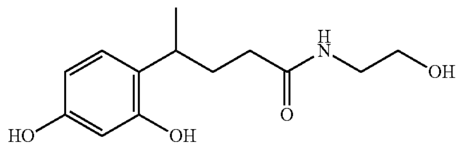 [SMILES: CC(CCC(=O)NCCO)c1ccc(O)cc1O] | 4-(2,4-dihydroxyphenyl)-N-(2-hydroxyethyl)pentanamide |
| 10 | 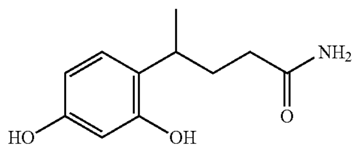 | 4-(2,4-dihydroxyphenyl)pentanamide |
| 11 | 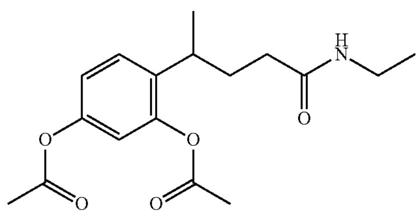 [SMILES: CCNC(=O)CCC(C)c1ccc(OC(C)=O)cc1OC(C)=O] | 4-[5-(ethylamino)-5-oxopentan-2-yl]benzene-1,3-diyl diacetate |
| 12 | 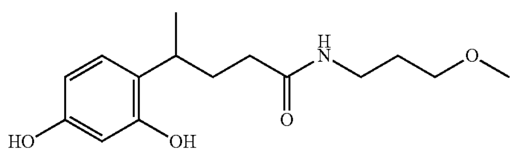 [SMILES: COCCCNC(=O)CCC(C)c1ccc(O)cc1O] | 4-(2,4-dihydroxyphenyl)-N-(3-methoxypropyl)pentanamide |
| 13 | 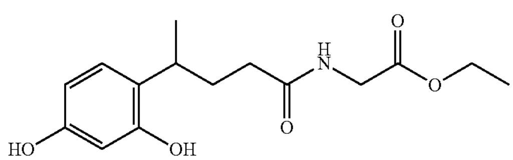 [SMILES: CCOC(=O)CNC(=O)CCC(C)c1ccc(O)cc1O] | ethyl N-[4-(2,4-dihydroxyphenyl)pentanoyl]glycinate |
| 14 | 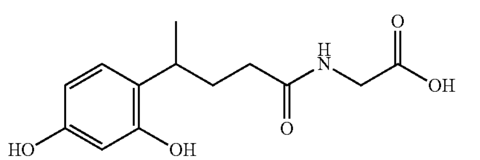 [SMILES: CC(CCC(=O)NCC(=O)O)c1ccc(O)cc1O] | N-[4-(2,4-dihydroxyphenyl)pentanoyl]glycine |
| 15 | 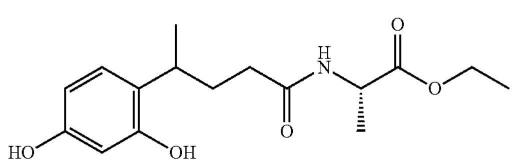 [SMILES: CCOC(=O)[C@H](C)NC(=O)CCC(C)c1ccc(O)cc1O] | ethyl N-[4-(2,4-dihydroxyphenyl)pentanoyl]-L-alaninate |
| 16 | 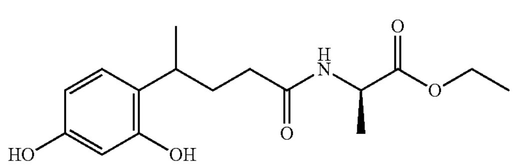 [SMILES: CCOC(=O)[C@@H](C)NC(=O)CCC(C)c1ccc(O)cc1O] | ethyl N-[4-(2,4-dihydroxyphenyl)pentanoyl]-D-alaninate |

TABLE 1-continued

The numbers in the table correspond to the numbers used in the examples below.

| Compound No. | Structure | Chemical name |
|---|---|---|
| 17 | 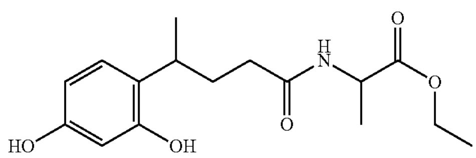 [SMILES: CCOC(=O)C(C)NC(=O)CCC(C)c1ccc(O)cc1O] | Ethyl N-[4-(2,4-dihydroxyphenyl)pentanoyl] DL alaninate |
| 18 | 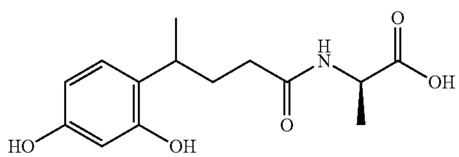 [SMILES: CC(CCC(=O)N[C@H](C)C(=O)O)c1ccc(O)cc1O] | N-[4-(2,4-dihydroxyphenyl)pentanoyl]-D-alanine |
| 19 | 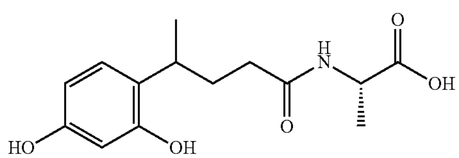 [SMILES: CC(CCC(=O)N[C@@H](C)C(=O)O)c1ccc(O)cc1O] | N-[4-(2,4-dihydroxyphenyl)pentanoyl]-L-alanine |
| 20 | 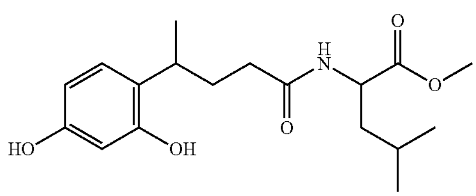 [SMILES: COC(=O)C(CC(C)C)NC(=O)CCC(C)c1ccc(O)cc1O] | methyl N-[4-(2,4-dihydroxyphenyl)pentanoyl]leucinate |
| 21 | 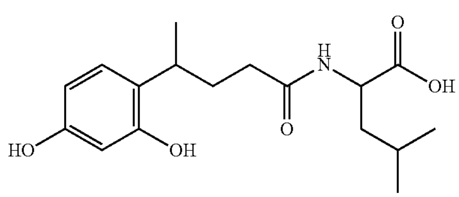 [SMILES: CC(C)CC(NC(=O)CCC(C)c1ccc(O)cc1O)C(=O)O] | N-[4-(2,4-dihydroxyphenyl)pentanoyl]leucine |
| 22 | 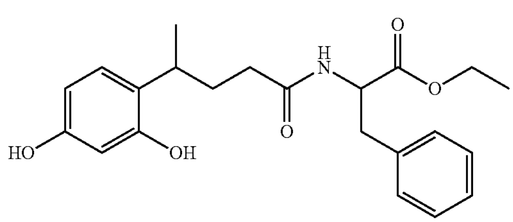 [SMILES: CCOC(=O)C(Cc1ccccc1)NC(=O)CCC(C)c1ccc(O)cc1O] | ethyl N-[4-(2,4-dihydroxyphenyl)pentanoyl]phenylalaninate |
| 23 | 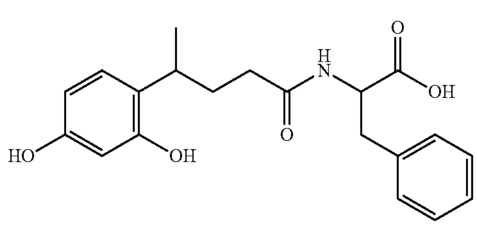 [SMILES: CC(CCC(=O)NC(Cc1ccccc1)C(=O)O)c1ccc(O)cc1O] | N-[4-(2,4-dihydroxyphenyl)pentanoyl]phenylalanine |

TABLE 1-continued

The numbers in the table correspond to the numbers used in the examples below.

| Compound No. | Structure | Chemical name |
|---|---|---|
| 24 | 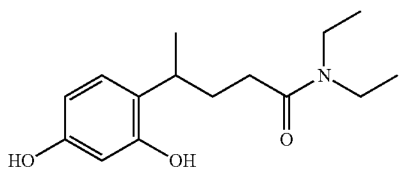 | 4-(2,4-dihydroxyphenyl)-N,N-diethylpentanamide |
| 25 | 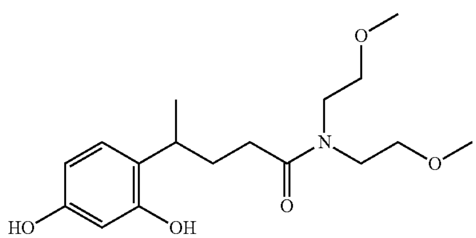 [SMILES: COCCN(CCOC)C(=O)CCC(C)c1ccc(O)cc1O] | 4-(2,4-dihydroxyphenyl)-N,N-bis(2-methoxyethyl)pentanamide |
| 26 | 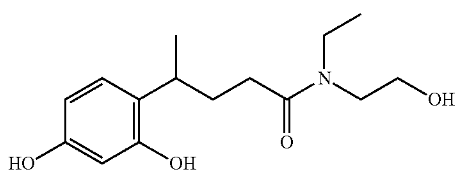 [SMILES: CCN(CCO)C(=O)CCC(C)c1ccc(O)cc1O] | 4-(2,4-dihydroxyphenyl)-N-ethyl-N-(2-hydroxyethyl)pentanamide |
| 27 | 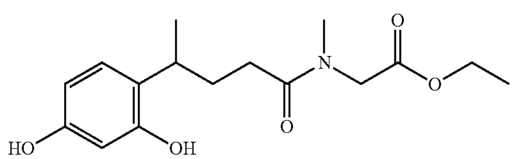 [SMILES: CCOC(=O)CN(C)C(=O)CCC(C)c1ccc(O)cc1O] | ethyl N-[4-(2,4-dihydroxyphenyl)pentanoyl]-N-methylglycinate |
| 28 | 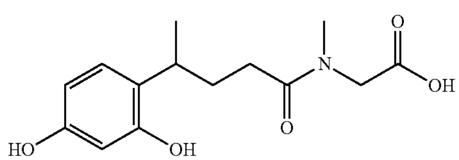 | N-[4-(2,4-dihydroxyphenyl)pentanoyl]-N-methylglycine |
| 29 | 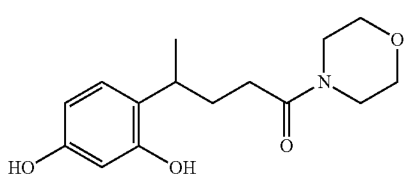 [SMILES: CC(CCC(=O)N1CCOCC1)c1ccc(O)cc1O] | 4-(2,4-dihydroxyphenyl)-1-(morpholin-4-yl)pentan-1-one |
| 30 | 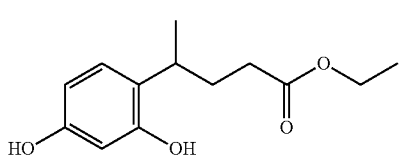 | ethyl 4-(2,4-dihydroxyphenyl)pentanoate |
| 31 | 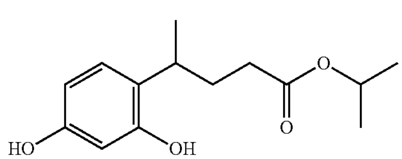 | propan-2-yl 4-(2,4-dihydroxyphenyl)pentanoate |

TABLE 1-continued

The numbers in the table correspond to the numbers used in the examples below.

| Compound No. | Structure | Chemical name |
|---|---|---|
| 32 | 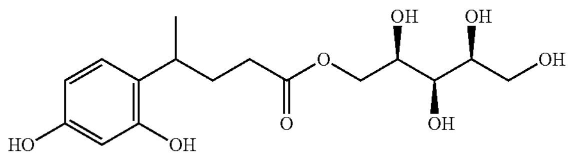 [SMILES: CC(CCC(=O)OC[C@@H](O)[C@H](O)[C@@H](O)CO)c1ccc(O)cc1O] | 5-O-[4-(2,4-dihydroxyphenyl)pentanoyl]-D-xylitol |
| 33 | 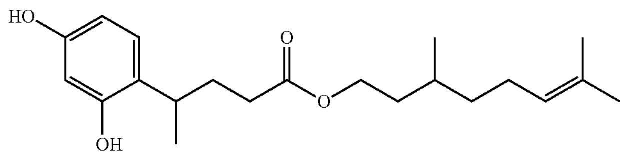 [SMILES: CC(C)=CCCC(C)CCOC(=O)CCC(C)c1ccc(O)cc1O] | 3,7-dimethyloct-6-en-1-yl 4-(2,4-dihydroxyphenyl)pentanoate |
| 34 | | 3-{[(2,2,5,5-tetramethyl-1,3-dioxan-4-yl)carbonyl]amino}propyl 4-(2,4-dihydroxyphenyl)pentanoate | and also the salts thereof, the solvates thereof and the optical and/or geometrical isomers thereof, including enantiomers and diastereoisomers, and the racemic mixtures thereof, alone or as a mixture.

A subject of the invention is in particular the compounds 2 to 34 and also the salts thereof, the solvates thereof and the optical and/or geometrical isomers thereof, including enantiomers and diastereoisomers, the racemic mixtures thereof, alone or as a mixture, described previously, and more particularly the compounds 2 to 11, 14, 15, 17, 18, 20, 22, 24 to 30, 32 and 34.

Compositions

A subject of the invention is also a cosmetic composition comprising, in a physiologically acceptable medium, at least one compound of formula (I) as described previously.

The composition according to the invention preferably contains at least one compound chosen from the compounds 1 to 34 described previously, and more particularly at least one compound chosen from the compounds 1 to 11, 14, 15, 17, 18, 20, 22, 24 to 30, 32 and 34.

In particular, a subject of the invention is also a composition, in particular a cosmetic composition, containing at least one compound of formula (I) as described previously, with the exception of the compound 1 described previously.

The composition according to the invention contains in particular at least one compound chosen from the compounds 2 to 34 described previously, and more particularly at least one compound chosen from the compounds 2 to 11, 14, 15, 17, 18, 20, 22, 24 to 30, 32 and 34.

The compounds of formula (I) according to the invention find a most particular application in the cosmetic field.

The composition according to the invention is preferably a cosmetic composition, that is to say a composition comprising a physiologically acceptable medium, and a compound of formula (I) as described previously.

The term "physiologically acceptable medium" is intended to mean a medium that is compatible with human keratin materials such as the skin of the body or of the face, the lips, the mucous membranes, the eyelashes, the nails, the scalp and/or the hair.

The compound (I) may be present in the composition according to the invention in an amount that may be between 0.01% and 10% by weight, preferably between 0.1% and 5% by weight, especially between 0.5% and 3% by weight, relative to the total weight of the composition.

The composition according to the invention is advantageously a cosmetic composition and may comprise adjuvants usually used in the cosmetic field.

Mention may be made especially of water; organic solvents, especially C2-C6 alcohols; oils, especially hydrocarbon-based oils and silicone oils; waxes, pigments, fillers, dyes, surfactants, emulsifiers; cosmetic active agents, organic or inorganic photoprotective agents, polymers, thickeners, preserving agents, fragrances, bactericides, ceramides, odour absorbers, antioxidants.

These optional cosmetic adjuvants may be present in the composition in a proportion of from 0.001% to 99.99% by weight, preferably 0.5% to 99% by weight, in particular from 0.1% to 98% by weight relative to the total weight of the composition. In any event, these adjuvants, and the proportions thereof, will be chosen by those skilled in the art such that the advantageous properties of the compounds according to the invention are not, or are not substantially, adversely affected by the envisaged addition.

As cosmetic active agents, it will be advantageous to introduce into the composition according to the invention at least one compound chosen from: desquamating agents; calmatives, moisturising agents; depigmenting agents different from the compounds of the invention; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; dermo-decontracting agents; tensioning agents; anti-pollution agents and/or free-radical scavengers; agents acting on the microcirculation; agents acting on the energy metabolism of cells; and mixtures thereof.

The composition according to the invention may be in any galenical form normally used in the cosmetic field, and especially in the form of an aqueous or aqueous-alcoholic solution, which is optionally gelled, a dispersion of the lotion type, which is optionally a two-phase lotion, an oil-in-water or water-in-oil or multiple (for example W/O/W or O/W/O) emulsion, an aqueous gel, a dispersion of oil in an aqueous phase by means of spherules, these spherules possibly being polymer nanoparticles such as nanospheres and nanocapsules or, better still, lipid vesicles of the ionic and/or nonionic type; aqueous or oily gels. These compositions are prepared according to the usual methods.

The composition according to the invention may constitute a skincare composition, and especially a cleansing, protecting, treating or care cream for the face, the hands, the feet, the major anatomical folds or the body (for example day creams, night creams, makeup-removing creams, foundation creams or anti-sun creams); a fluid foundation, a makeup-removing milk, a protective or care body milk or an anti-sun milk; a skincare lotion, gel or mousse, such as a cleansing lotion.

Process

A subject of the invention is also a non-therapeutic cosmetic process for depigmenting, lightening and/or bleaching keratin materials, in particular the skin, comprising the application of the composition described previously. More preferably, it is the process for depigmenting, lightening and/or bleaching the skin.

A subject of the invention is also a non-therapeutic cosmetic process for depigmenting, lightening and/or bleaching keratin materials, in particular the skin, comprising the application to the skin of at least one compound of formula (I) as defined previously, in particular of at least one compound chosen from the compounds 1 to 34 described previously, and more particularly of at least one compound chosen from the compounds 1 to 11, 14, 15, 17, 18, 20, 22, 24 to 30, 32 and 34.

In particular, a subject of the invention is a non-therapeutic cosmetic process for depigmenting, lightening and/or bleaching keratin materials, in particular the skin, comprising the application to the skin of at least one compound chosen from the compounds of formula (I) as defined previously, with the exception of the compound 1 described previously, in particular of at least one compound chosen from the compounds 2 to 34 described previously, and more particularly of at least one compound chosen from the compounds 2 to 11, 14, 15, 17, 18, 20, 22, 24 to 30, 32 and 34.

The invention also relates to the non-therapeutic cosmetic use of at least one compound of formula (I) as defined below, as an agent for bleaching, lightening and/or depigmenting keratin materials, in particular the skin.

In particular, the invention relates to the non-therapeutic cosmetic use of at least one compound chosen from the compounds 1 to 34 described previously, and more particularly at least one compound chosen from the compounds 1 to 11, 14, 15, 17, 18, 20, 22, 24 to 30, 32 and 34 as an agent for bleaching, lightening and/or depigmenting keratin materials, in particular the skin.

Preferably, the invention relates to the non-therapeutic cosmetic use of at least one compound chosen from the compounds 2 to 34 described previously, and more particularly at least one compound chosen from the compounds 2 to 11, 14, 15, 17, 18, 20, 22, 24 to 30, 32 and 34 as an agent for bleaching, lightening and/or depigmenting keratin materials, in particular the skin.

EXAMPLE

The invention is illustrated in greater detail by the following non-limiting examples.

Example 1: Synthesis of Compound No. 1: 4-(2,4-dihydroxyphenyl)pentanoic Acid

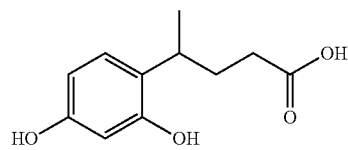

This compound is described in the article R Gopal; P Gupta Synthesis of succin-as-eins; Bulletin of the Chemical Society of Japan, 47, 7, 1789-1790.

The MS and NMR spectra are in accordance with the desired product and the compound is stable.

Example 2: Synthesis of Compound No. 2: 4-(2,4-dihydroxyphenyl)-N-ethylpentanamide

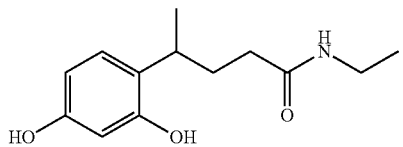

Synthesis of compound 2: To a solution of compound 1 (3.45 g, 16.4 mmol) and of ethylamine hydrochloride (2.0 g, 24.5 mmol) in 50 ml of DMF were added DMAP (3.6 g, 29.5 mmol) and EDCI (3.8 g, 19.8 mmol). The reaction mixture was stirred at ambient temperature for 15 h. The mixture was then poured into 300 ml of water and extracted three times with EtOAc. The combined organic phases were washed with water three times and concentrated to dryness. The crude product was purified by silica gel column chromatography, eluting with $CH_2Cl_2$:MeOH=10:1 to give 1.99 g of compound 2 in the form of a yellow solid with a yield of 51%. The MS and NMR spectra are in accordance with the desired product.

Example 3: Synthesis of Compound No. 3/4-(2,4-dihydroxyphenyl)-N-(propan-2-yl)pentanamide

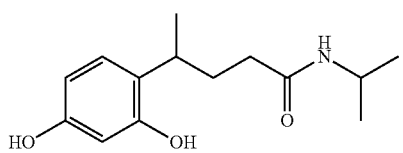

Synthesis of compound 3: To a solution of compound 1 (1.05 g, 5.0 mmol) in 20 ml of DMF were added EDCI (1.24 g, 6.5 mmol), DMAP (0.12 g, 1.0 mmol) and isopropylamine (0.52 ml, 6.0 mmol) in sequence at 0° C. After stirring at ambient temperature for 20 h, the mixture was adjusted to pH=7 using 3N HCl. The solution was then poured into water and extracted twice with ethyl acetate. The combined extracts were washed with water and brine, dried over sodium sulfate and evaporated. The resulting residue was purified by silica gel chromatography (CH₂Cl₂/MeOH=40:1) to give 0.3 g of compound. The resulting residue was purified by silica gel chromatography (CH₂Cl₂/MeOH=40:1) to give 0.3 g of compound 3 in the form of a pale yellow solid with a yield of 24%. Mp: 60-65° C.

The MS and NMR spectra are in accordance with the desired product.

Example 4: Synthesis of Compound No. 4/N-butyl-4-(2,4-dihydroxyphenyl)pentanamide

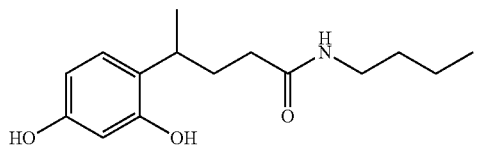

To a solution of compound 1 (1.0 g, 4.76 mmol) and of butylamine hydrochloride (427 mg, 5.7 mmol) in 20 ml of DMF were added DMAP (cat.) and EDCI (1.1 g, 5.7 mmol). The reaction mixture was stirred at ambient temperature for 15 h. The mixture was then poured into 300 ml of water and extracted three times with EtOAc. The combined organic phases were washed with water three times and concentrated to dryness. The crude product was purified by silica gel column chromatography, eluting with CH₂Cl₂:MeOH=10:1 to give 605 mg of compound 4 in the form of a yellow solid with a yield of 48%. m.p.: 76□.

The MS and NMR spectra are in accordance with the desired product.

Example 5: Synthesis of Compound No. 5/N-(butan-2-yl)-4-(2,4-dihydroxyphenyl)pentanamide

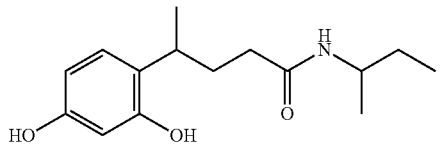

To a solution of compound 1 (692 mg, 3.6 mmol) in 10 ml of THF was added butan-2-amine (293 mg, 4 mmol). The mixture was stirred at ambient temperature for 16 h. The solvent was removed under reduced pressure. The resulting residue was purified by silica gel chromatography (eluent: EtOAc/PE=1/2) to give 470 mg of compound 5 in the form of a white solid with a yield of 49%.

The MS and NMR spectra are in accordance with the desired product.

Example 6: Synthesis of Compound No. 6/N-cyclohexyl-4-(2,4-dihydroxyphenyl)pentanamide

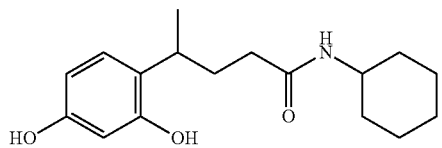

Synthesis of the compound F':

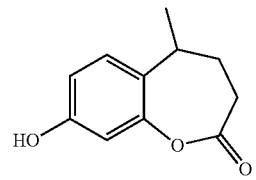

To a solution of compound 1 (3.2 g, 15.2 mmol) in 40 ml of DMF were added EDCI (3.78 g, 19.8 mmol) and DMAP (0.46 g, 3.8 mmol) in sequence at 0° C. After stirring at ambient temperature for 20 h, the mixture was adjusted to pH=7 using 3N HCl. The solution was then poured into water and extracted twice with ethyl acetate.

The combined extracts were washed with water and brine, dried over sodium sulfate and evaporated. The resulting residue was purified by silica gel chromatography (PE/EA=5:1) to give 2.5 g of compound F' in the form of a white solid with a yield of 86%. Melting point: 63-67° C.

Synthesis of compound 6: To a solution of compound F' (650 mg, 3.38 mmol) in 20 ml of THF was added cyclohexylamine (396 mg, 4.0 mmol). The reaction mixture was heated at 50° C. for 8 h. The mixture was cooled to ambient temperature. The mixture was then poured into 200 ml of water and extracted three times with EtOAc. The combined organic phases were washed with water three times and concentrated to dryness under vacuum. The crude product was purified by silica gel column chromatography, eluting with CH₂Cl₂:MeOH=50:1 to give 800 mg of compound 6 in the form of a white solid with a yield of 80%. Mp. 75-78□.

The MS and NMR spectra are in accordance with the desired product.

Example 7: Synthesis of Compound No. 7/N-(cyclohexylmethyl)-4-(2,4-dihydroxyphenyl)pentanamide

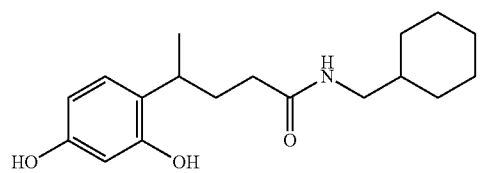

To a solution of compound F' (692 mg, 3.6 mmol) (0.5 g, 2.6 mmol) in 15 ml of THF was added aminomethylcyclohexane (0.4 ml, 3.1 mmol). After stirring at ambient temperature for 20 h, the solvent was removed under vacuum. The resulting residue was purified by silica gel chromatography ($CH_2Cl_2$/MeOH=40:1) to give 0.4 g of compound 7 in the form of a white solid with a yield of 50%.

The MS and NMR spectra are in accordance with the desired product.

Example 8: Synthesis of Compound No. 8/4-(2,4-dihydroxyphenyl)-N-[2-(4-hydroxyphenyl)ethyl]pentanamide

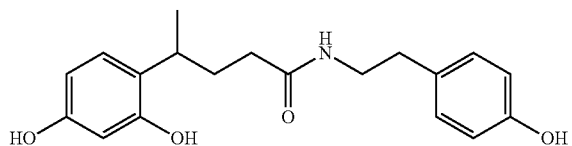

8

To a solution of compound 1 (690 mg, 3.2 mmol) and of 4-(2-aminoethyl)phenol (527 mg, 3.8 mmol) in 20 ml of DMF were added DMAP (cat.) and EDCI (730 mg, 3.8 mmol). The reaction mixture was stirred at ambient temperature for 15 h. The mixture was then poured into 300 ml of water and extracted three times with EtOAc. The organic phase was washed with water three times and concentrated to dryness. The crude product was purified by silica gel column chromatography, eluting with $CH_2Cl_2$:MeOH=10:1 to give 700 mg of compound 8 in the form of a yellow solid with a yield of 67%. m.p.: 135□.

The MS and NMR spectra are in accordance with the desired product.

Example 9: Synthesis of Compound No. 9/4-(2,4-dihydroxyphenyl)-N-(2-hydroxyethyl)pentanamide

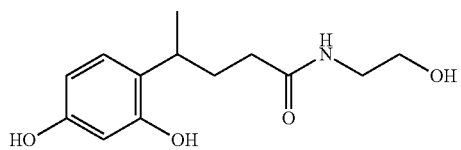

9

To a solution of compound F' (0.5 g, 2.6 mmol) in 15 ml of THF was added ethanolamine (0.19 ml, 3.1 mmol). After having stirred at 80° C. for 20 h, the mixture was poured into water and extracted two times with ethyl acetate. The combined extracts were washed with water and brine, dried over sodium sulfate and evaporated under vacuum. The residue was purified by silica gel chromatography ($CH_2Cl_2$/MeOH=40:1 to 15:1) to give 0.5 g of compound 9 in the form of a pale pink oil with a yield of 76%.

The MS and NMR spectra are in accordance with the desired product.

Example 10: Synthesis of Compound No. 10/4-(2,4-dihydroxyphenyl)pentanamide

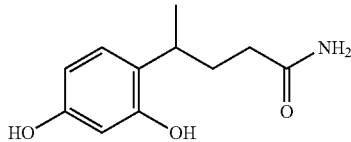

10

To a solution of compound F' (800 mg, 4.16 mmol) in 20 ml of THF was added $NH_3H_2O$ (350 mg, 10.0 mmol). The reaction mixture was stirred at ambient temperature for 2 h. The mixture was then poured into 200 ml of water and extracted three times with EtOAc. The combined organic phases were washed with water three times and concentrated to dryness under vacuum. The crude product was further purified by silica gel column chromatography, eluting with $CH_2Cl_2$:MeOH=50:1 to give 650 mg of compound 10 in the form of a white solid with a yield of 75%. MP. 54-56□

The MS and NMR spectra are in accordance with the desired product.

Example 11: Synthesis of Compound No. 11/4-[5-(ethylamino)-5-oxopentan-2-yl]benzene-1,3-diyl diacetate

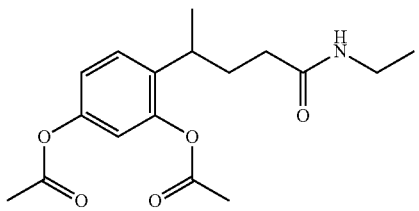

11

To a solution of compound 2 (0.57 g, 2.4 mmol) in 40 ml of THF was added TEA (0.72 g, 7.2 mmol), followed by slow deposit of acetyl chloride (0.56 g, 7.2 mmol) into the mixture at 0° C. in an ice bath. The mixture was stirred at ambient temperature for 16 h. The mixture was concentrated under reduced pressure. The resulting residue was purified by silica gel chromatography (eluent: 3/1 petroleum ether/ethyl acetate) to give 0.48 g of compound 11 in the form of a white powder with a yield of 62%.

The MS and NMR spectra are in accordance with the desired product.

Example 12: Synthesis of Compound No. 12/4-(2,4-dihydroxyphenyl)-N-(3-methoxypropyl)pentanamide

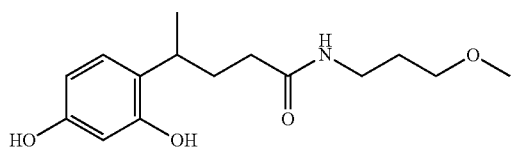

12

To a solution of compound 1 (1.1 g, 5.2 mmol) in 20 ml of DMF were added EDCI (1.3 g, 6.8 mmol), DMAP (0.13 g, 1.05 mmol) and 3-methoxypropylamine (0.64 ml, 6.3 mmol) in sequence at 0° C. After stirring at ambient temperature for 20 h, the mixture was adjusted to pH=7 using 3N HCl. The solution was then poured into water and extracted twice with ethyl acetate. The combined extracts were washed with water and brine, dried over sodium sulfate and evaporated. The resulting residue was purified by silica gel chromatography ($CH_2Cl_2$/MeOH=40:1) to give 0.4 g of compound 12 in the form of a pale pink oil with a yield of 27%.

The MS and NMR spectra are in accordance with the desired product.

Example 13: Synthesis of Compound No. 13/ethyl N-[4-(2,4-dihydroxyphenyl)pentanoyl]glycinate

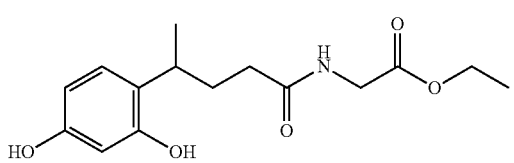

13

To a solution of compound F' (2.1 g, 10.9 mmol) in 40 ml of DMF were added glycine ethyl ester hydrochloride (1.8 g, 13.1 mmol) and triethylamine (2.1 mg, 14.2 mmol). After stirring at 90° C. for 20 h, the mixture was filtered. The filtrate was poured into water and extracted twice with ethyl acetate. The combined extracts were washed with water and brine, dried over sodium sulfate and evaporated under vacuum. The residue was purified by silica gel chromatography (dichloromethane/methanol=60:1) to give 1.3 g of compound 3 in the form of a yellow solid with a yield of 41%. Mp: 56° C.

The MS and NMR spectra are in accordance with the desired product.

Example 14: Synthesis of Compound No. 14/N-[4-(2,4-dihydroxyphenyl)pentanoyl]glycine

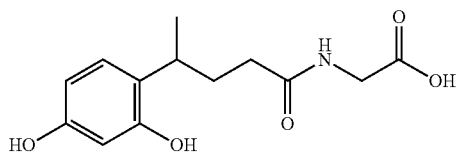

14

To a solution of compound 13 (1.22 g, 4.1 mmol) in 30 ml of acetonitrile were added $K_2CO_3$ (1.3 g, 9.5 mmol) and benzyl bromide (1.1 ml, 9.1 mmol). After stirring at reflux for 20 h, the mixture was filtered and evaporated under vacuum. The residue was purified by silica gel chromatography (petroleum ether/ethyl acetate=6:1) to give 1.83 g of an intermediate benzylated ethyl ester in the form of a white solid with a yield of 95%.

A solution of this benzylated intermediate (1.83 g, 3.85 mmol) in 30 ml of methanol was added to a solution of $LiOH \cdot H_2O$ (0.22 g, 5.4 mmol) in 2 ml of water at 0° C. The mixture was stirred at ambient temperature for 20 h. The mixture was then adjusted to pH=6 using HCl and concentrated under vacuum. The residue was purified by silica gel chromatography (dichloromethane/methanol=40:1) to give 1.2 g of benzylated acid intermediate in the form of a yellow solid with a yield of 65%.

To a solution of benzylated acid intermediate (1.6 g, 3.6 mmol) in 20 ml of methanol was added 0.3 g of Pd/C. The mixture was stirred at ambient temperature under hydrogen for 20 h. The mixture was filtered. The filtrate was concentrated under vacuum. The residue was purified by silica gel chromatography (dichloromethane/methanol=40:1) to give 0.45 g of compound 14 in the form of a white solid with a yield of 47%. Mp: 59-65° C.

The MS and NMR spectra are in accordance with the desired product.

Example 15: Synthesis of Compound No. 15/ethyl N-[4-(2,4-dihydroxyphenyl)pentanoyl]-L-alaninate

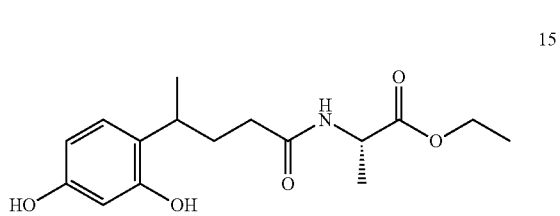 [SMILES: CCOC(=O)[C@H](C)NC(=O)CCC(C)c1ccc(O)cc1O]

15

To a solution of compound F' (768 mg, 4.0 mmol) and L-alanine ethyl ester hydrochloride (L-alanine: (S)-2-aminopropionic acid; CAS: 1115 to 59-9) (675 mg, 4.4 mmol) in 20 ml of DMF was added TEA (253 mg, 2.5 mmol). The reaction mixture was heated at 80° C. for 15 h. The mixture was cooled to ambient temperature. The mixture was then poured into 200 ml of water and extracted three times with EtOAc. The combined organic layers were washed with water three times and concentrated to dryness under vacuum. The crude product was further purified by silica gel column chromatography, eluting with $CH_2Cl_2$:MeOH=50:1 to give 742 mg of compound 15 in the form of a yellow solid with a yield of 60%. Mp: 48-50° C.

The MS and NMR spectra are in accordance with the desired product.

Example 16: Synthesis of Compound No. 16/ethyl N-[4-(2,4-dihydroxyphenyl)pentanoyl]-D-alaninate

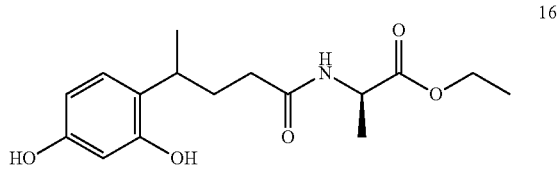 [SMILES: CCOC(=O)[C@@H](C)NC(=O)CCC(C)c1ccc(O)cc1O]

16

To a solution of compound F' (768 mg, 4.0 mmol) and D-alanine ethyl ester hydrochloride (D-alanine: (R)-2-aminopropionic acid; CAS: 6331-09-5) (675 mg, 4.4 mmol) in 20 ml of DMF was added TEA (253 mg, 2.5 mmol). The reaction mixture was heated at 80° C. for 15 h. The mixture was cooled to ambient temperature. The mixture was then poured into 200 ml of water and extracted three times with EtOAc. The combined organic layers were washed with water three times and concentrated to dryness under vacuum. The crude product was further purified by silica gel column chromatography, eluting with $CH_2Cl_2$:MeOH=50:1 to give 650 mg of compound 16 in the form of a yellow solid with a yield of 60%.

The MS and NMR spectra are in accordance with the desired product.

Example 17: Synthesis of Compound No. 17/ethyl N-[4-(2,4-dihydroxyphenyl)pentanoyl]-DL-alaninate

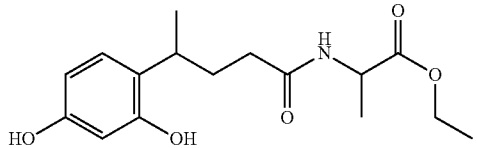

17

To a solution of compound F' (430 mg, 2.2 mmol) and alanine hydrochloride (384 mg, 2.5 mmol) in 20 ml of DMF was added TEA (253 mg, 2.5 mmol). The reaction mixture was heated at 80° C. for 15 h. The mixture was cooled to ambient temperature. The mixture was then poured into 200 ml of water and extracted three times with EtOAc. The combined organic layers were washed with water three times and concentrated to dryness under vacuum. The crude product was further purified by silica gel column chromatography, eluting with $CH_2Cl_2$:MeOH=50:1 to give 544 mg of compound 17 in the form of a yellow solid with a yield of 80%. P.p.45-48° C.

The MS and NMR spectra are in accordance with the desired product.

Example 18: Synthesis of Compound No. 18/N-[4-(2,4-dihydroxyphenyl)pentanoyl]-D-alanine

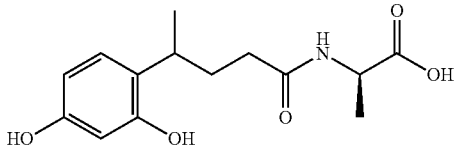

18

To a solution of compound 15 (1.55 g, 5.0 mmol) in 60 ml of MeCN were added $K_2CO_3$ (1.73 g, 12.5 mmol) and BnBr (1.88 g, 11.0 mmol). The reaction mixture was refluxed for 15 h. After cooling to ambient temperature, the mixture was filtered and the filtrate was concentrated to dryness. The resulting residue was purified by silica gel column chromatography using dichloromethane, to give 2.3 g of intermediate benzylated ester in the form of a white powder with a yield of 93%.

To a solution of the benzylated ester intermediate (2.3 g, 4.7 mmol) in 50 ml of THF was added LiOH (236 mg, 5.6 mmol) in 8.0 ml of water. The reaction mixture was stirred for 15 h. 200 ml of water were poured into the mixture and said mixture was acidified with 6N HCl at pH=2, and the resulting mixture was extracted twice with EtOAc. The combined organic layer was washed with water three times and concentrated to dryness. The resulting residue was purified by silica gel chromatography (dichloromethane/methanol=500:2) to give 1.7 g of benzylated acid intermediate in the form of a white powder with a yield of 77%.

A mixture of benzylated acid intermediate (1.5 g, 3.3 mmol) and 400 mg of 10% of Pd/C in 60 ml of MeOH was stirred under hydrogen at ambient temperature for 15 h. The reaction mixture was filtered and the filtrate was concentrated to dryness. The resulting residue was purified by silica gel chromatography (dichloromethane/methanol=250:1) to give 795 mg of compound 18 in the form of a white powder with a yield of 87%. Mp: 65 to 68□.

The MS and NMR spectra are in accordance with the desired product.

Example 19: Synthesis of Compound No. 19/N-[4-(2,4-dihydroxyphenyl)pentanoyl]-L-alanine

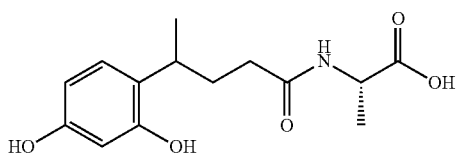

19

To a solution of compound 16 (1.55 g, 5.0 mmol) in 60 ml of MeCN were added $K_2CO_3$ (1.73 g, 12.5 mmol) and BnBr (1.88 g, 11.0 mmol). The reaction mixture was refluxed for 15 h. After cooling to ambient temperature, the mixture was filtered and the filtrate was concentrated to dryness. The resulting residue was purified by silica gel column chromatography using dichloromethane, to give 2.35 g of intermediate benzylated ester in the form of white powder with a yield of 96%.

To a solution of the benzylated ester intermediate (2.3 g, 4.7 mmol) in 50 ml of THF was added LiOH (236 mg, 5.6 mmol) in 8.0 ml of water. The reaction mixture was stirred for 15 h. 200 ml of water were poured into the mixture and said mixture was acidified with 6N HCl at pH=2, and the resulting mixture was extracted twice with EtOAc. The combined organic layer was washed with water three times and concentrated to dryness. The resulting residue was purified by silica gel chromatography (dichloromethane/methanol=500:2) to give 1.4 g of benzylated acid intermediate in the form of a white powder with a yield of 62%.

A mixture of benzylated acid intermediate (1.3 g, 2.8 mmol) and 400 mg of 10% Pd/C in 60 ml of MeOH was stirred under hydrogen at ambient temperature for 15 h. The reaction mixture was filtered and the filtrate was concentrated to dryness. The resulting residue was purified by silica gel chromatography, (dichloromethane/methanol=250:1) to give 578 mg of compound 19 in the form of a white powder with a yield of 73%.

The MS and NMR spectra are in accordance with the desired product.

Example 20: Synthesis of Compound No. 20/methyl N-[4-(2,4-dihydroxyphenyl)pentanoyl]leucinate

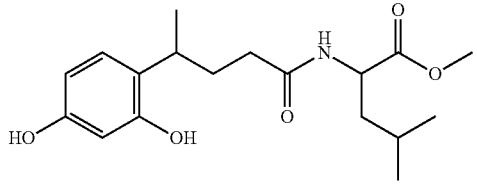

20

To a solution of compound 1 (3.15 g, 15 mmol) in 80 ml of DMF were added D-leucine methacrylate hydrochloride (CAS: 5845-53-4) (3.27 g, 18 mmol), EDCI (3.46 g, 18 mmol), HOBt (2.43 g, 18 mmol) and TEA (5.25 ml, 36 mmol). The mixture was stirred at ambient temperature for 15 h. 200 ml of water were then added to the mixture and extracted three times with ethyl acetate. The organic layers were dried over sodium sulfate and filtered. The filtrate was concentrated under reduced pressure. The resulting residue was purified by silica gel chromatography (eluent: 50/1 dichloromethane/methanol) to give 3.6 g of compound 20 in the form of a white powder with a yield of 71%.
Mp: 63° C.
The MS and NMR spectra are in accordance with the desired product.

Example 21: Synthesis of Compound No. 21/N-[4-(2,4-dihydroxyphenyl)pentanoyl]leucine

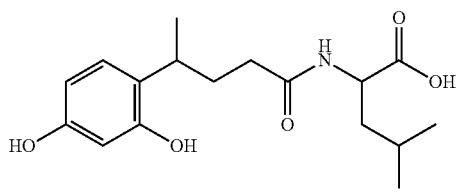

21

To a solution of compound 20 (4.2 g, 12.4 mmol) in 80 ml of acetonitrile were added $K_2CO_3$ (3.94 g, 28.5 mmol) and benzyl bromide (4.88 g, 28.5 mmol). After refluxing for 20 hours, the mixture was filtered. The filtrate was evaporated under vacuum. The residue was purified by silica gel chromatography (PE/EA=6:1) to give 4.18 g of benzylated ester intermediate as a pale yellow oil with a yield of 65%.
To a solution of it (4.18 g, 8.07 mmol) in 60 ml of THF was added a solution of $LiOH.H_2O$ (0.68 g, 16.14 mmol) in 10 ml of water at 0° C. The mixture was stirred at ambient temperature for 20 h. The mixture was then adjusted to pH=6 using HCl and concentrated under vacuum. The residue was purified by silica gel chromatography ($CH_2Cl_2$/MeOH=40:1) to give 2.2 g of benzylated acid intermediate as a pale yellow oil with a yield of 54%. Mp: 56-57° C.
To a solution of it (2.2 g, 4.37 mmol) in 60 ml of methanol was added 0.38 g of Pd/C. The mixture was stirred at ambient temperature under hydrogen for 20 h. The mixture was filtered using a diatomite. The filtrate was concentrated under vacuum. The residue was purified by silica gel chromatography (dichloromethane/methanol=25:1) to give 0.97 g of compound 21 in the form of a white solid with a yield of 69%.
The MS and NMR spectra are in accordance with the desired product.

Example 22: Synthesis of Compound No. 22/ethyl N-[4-(2,4-dihydroxyphenyl)pentanoyl]phenylalaninate

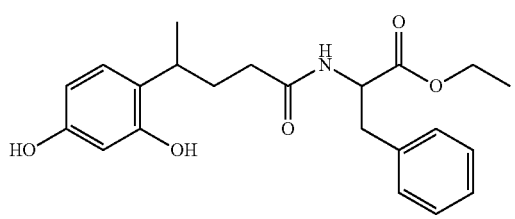

22

To a solution of compound 1 (0.6 g, 2.86 mmol) in 15 ml of DMF were added EDCI (0.71 g, 3.71 mmol), DMAP (0.52 g, 4.29 mmol) and ethylphenyl alaninate hydrochloride (0.79 g, 3.43 mmol) in sequence at 0° C. After stirring at ambient temperature for 20 h, the mixture was adjusted to pH=7 using 3N HCl. The solution was then poured into water and extracted twice with ethyl acetate. The combined extracts were washed with water and brine, dried over sodium sulfate and evaporated. The resulting residue was purified by silica gel chromatography ($CH_2Cl_2$/MeOH=50:1) to give 0.4 g of compound 22 in the form of a white solid with a yield of 36%. Mp: 51-59□.
The MS and NMR spectra are in accordance with the desired product.

Example 23: Synthesis of Compound No. 23/N-[4-(2,4-dihydroxyphenyl)pentanoyl]phenylalanine

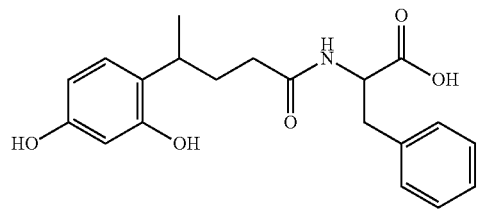

23

To a solution of compound 22 (1 g, 2.6 mmol) in 30 ml of acetonitrile were added $K_2CO_3$ (0.82 g, 6.0 mmol) and benzyl bromide (0.65 ml, 5.5 mmol). After stirring at reflux for 20 h, the mixture was filtered and the filtrated was evaporated under vacuum. The residue was purified by silica gel chromatography (PE/EA=6:1) to give 1.22 g of a pale yellow oil with a yield of 83%. Mp: 74-80° C. A solution of the latter (1.1 g, 1.95 mmol) in 15 ml of methanol was added to a solution of $LiOH.H_2O$ (0.11 g, 2.73 mmol) in 2 ml of water at 0° C. The mixture was stirred at ambient temperature for 20 h. The mixture was then adjusted to pH=6 using HCl and concentrated under vacuum. The residue was purified by silica gel chromatography ($CH_2Cl_2$/MeOH=40:1) to give 0.97 g of a pale yellow oil with a yield of 94%.
To a solution of this benzylated carboxylic acid (0.97 g, 1.8 mmol) in 20 ml of methanol was added 0.2 g of Pd/C. The mixture was stirred at ambient temperature under hydrogen for 15 h. The mixture was filtered using a diatomite. The filtrate was concentrated under vacuum. The residue was purified by silica gel chromatography (dichloromethane/methanol=25:1) to give 0.32 g of compound 23 in the form of a white solid with a yield of 50%.

The MS and NMR spectra are in accordance with the desired product.

Example 24: Synthesis of Compound No. 24/4-(2,4-dihydroxyphenyl)-N,N-diethylpentanamide

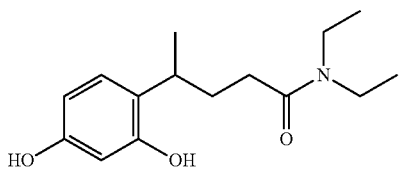

To a solution of compound F' (0.577 g, 3 mmol) in 40 ml of DMF was added diethylamine (0.342 g, 4.5 mmol). The mixture was heated to 90° C. and was reacted for 6 h. After cooling of the mixture, 100 ml of water were added to the mixture and the latter was extracted with ethyl acetate. The organic layers were dried over sodium sulfate and filtered. The filtrate was concentrated under reduced pressure. The resulting residue was purified by silica gel chromatography (eluent: 50/1 dichloromethane/methanol) to give 423 mg of compound 24 in the form of a pale yellow oil with a yield of 51%.

The MS and NMR spectra are in accordance with the desired product.

Example 25: Synthesis of Compound No. 25/4-(2,4-dihydroxyphenyl)-N,N-bis(2-methoxyethyl)pentanamide

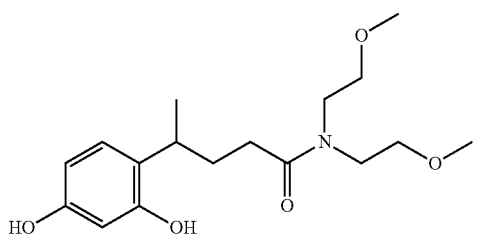

To a solution of compound F' (810 mg, 4.2 mmol) in 20 ml of DMF was added bis(2-methoxyethyl)amine (670 mg, 5.0 mmol). The reaction mixture was heated at 90° C. for 15 h. The mixture was cooled to ambient temperature. The mixture was then poured into 200 ml of water and extracted three times with EtOAc. The combined organic layers were washed with water three times and concentrated to dryness under vacuum. The crude product was further purified by silica gel column chromatography, eluting with $CH_2Cl_2$:MeOH=50/1 to give 330 mg of compound 25 in the form of a white solid with a yield of 23%. Mp: 78-81° C.

The MS and NMR spectra are in accordance with the desired product.

Example 26: Synthesis of Compound No. 26/4-(2,4-dihydroxyphenyl)-N-ethyl-N-(2-hydroxyethyl)pentanamide

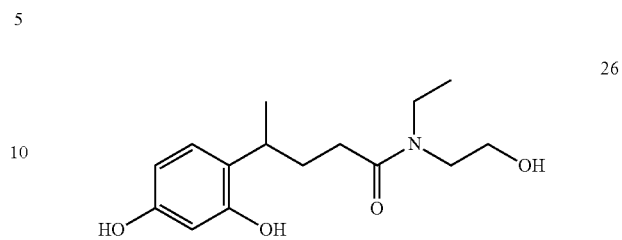

Synthesis of compound 26: To a solution of compound F' (1.92 g, 10 mmol) in 80 ml of DMF was added 2-(ethylamino)ethanol (1.34 g, 15 mmol). The mixture was heated to 120° C. and was reacted for 5 h. After cooling of the mixture, 150 ml of water were added to the mixture and the latter was extracted with ethyl acetate. The organic layers were dried over sodium sulfate and filtered. The filtrate was concentrated under reduced pressure. The resulting residue was purified by silica gel chromatography (eluent: 50/1 dichloromethane/methanol) to give 890 mg of compound 26 in the form of a white powder with a yield of 32%.

The MS and NMR spectra are in accordance with the desired product.

Example 27: Synthesis of Compound No. 27/ethyl N-[4-(2,4-dihydroxyphenyl)pentanoyl]-N-methylglycinate

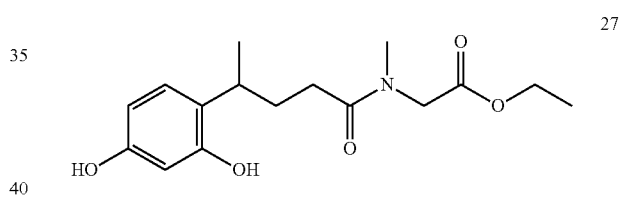

To a solution of compound F' (3.2 g, 15.2 mmol) in 40 ml of DMF were added EDCI (3.78 g, 19.8 mmol) and DMAP (0.46 g, 3.8 mmol) in sequence at 0° C. After stirring at ambient temperature for 20 h, the mixture was adjusted to pH=7 using 3N HCl. The solution was then poured into water and extracted twice with ethyl acetate. The combined extracts were washed with water and brine, dried over sodium sulfate and evaporated. The resulting residue was purified by silica gel chromatography (PE/EA=5:1) to give 2.5 g of compound 27 in the form of white solid with a yield of 86%.

The MS and NMR spectra are in accordance with the desired product.

Example 28: Synthesis of Compound No. 28/N-[4-(2,4-dihydroxyphenyl)pentanoyl]-N-methylglycine

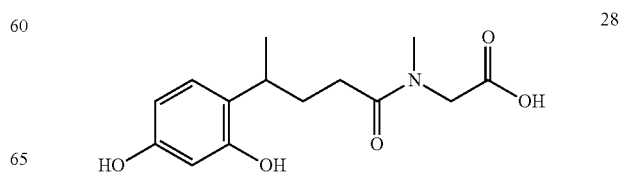

To a solution of compound 27 (1 g, 2.6 mmol) in 30 ml of acetonitrile were added K$_2$CO$_3$ (0.82 g, 6.0 mmol) and benzyl bromide (0.65 ml, 5.5 mmol). After stirring at reflux for 20 h, the mixture was filtered and the filtrated was evaporated under vacuum. The residue was purified by silica gel chromatography (PE/EA=6:1) to give 1.22 g of a pale yellow oil with a yield of 83%. A solution of the latter (1.1 g, 1.95 mmol) in 15 ml of methanol was added to a solution of LiOH.H$_2$O (0.11 g, 2.73 mmol) in 2 ml of water at 0° C. The mixture was stirred at ambient temperature for 20 h. The mixture was then adjusted to pH=6 using HCl and concentrated under vacuum. The residue was purified by silica gel chromatography (CH$_2$Cl$_2$/MeOH=40:1) to give 0.97 g of a pale yellow oil with a yield of 94%. To a solution of the latter (0.97 g, 1.8 mmol) in 20 ml of methanol was added 0.2 g of Pd/C. The mixture was stirred at ambient temperature under hydrogen for 15 h. The mixture was filtered using a diatomite. The filtrate was concentrated under vacuum. The residue was purified by silica gel chromatography (dichloromethane/methanol=25:1) to give 0.32 g of compound 28 in the form of a white solid with a yield of 50%.

The MS and NMR spectra are in accordance with the desired product.

Example 29: Synthesis of Compound No. 29/4-(2, 4-dihydroxyphenyl)-1-(morpholin-4-yl)pentan-1-one

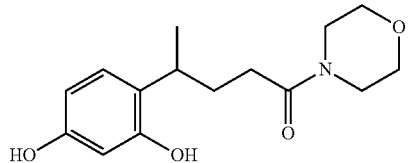

29

To a solution of compound F' (846 mg, 4.4 mmol) in 10 ml of THF was added morpholine (401 mg, 4.6 mmol). The mixture was stirred at a.t. for 16 h. The solvent was removed under reduced pressure. The resulting residue was purified by silica gel chromatography (eluent: EtOAc/PE=1/2) to give 700 mg of compound 29 in the form of a white solid with a yield of 57%.

The MS and NMR spectra are in accordance with the desired product.

Example 30: Synthesis of Compound No. 30/ethyl 4-(2,4-dihydroxyphenyl)pentanoate

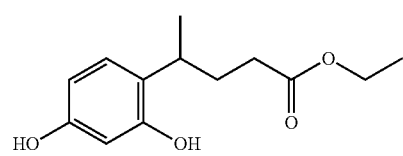

30

To a solution of compound 1 (500 mg, 2.3 mmol) in 20 ml of ethanol were added drops of sulfuric acid. The mixture was stirred at a.t. for 18 h. The solvent was removed under reduced pressure. The resulting residue was purified by silica gel chromatography (eluent: EtOAc/PE=1/2) to give 437 mg of compound 30 in the form of an oil with a yield of 88%.

The MS and NMR spectra are in accordance with the desired product.

Example 31: Synthesis of Compound No. 31/propan-2-yl 4-(2,4-dihydroxyphenyl)pentanoate

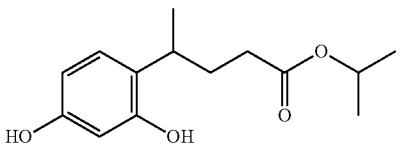

31

The same procedure as for compound 30 using isopropanol at 80° C. gives compound 31 in the form of an oil with a yield of 95%

The MS and NMR spectra are in accordance with the desired product.

Example 32: Synthesis of Compound No. 32/5-O-[4-(2,4-dihydroxyphenyl)pentanoyl]-D-xylitol

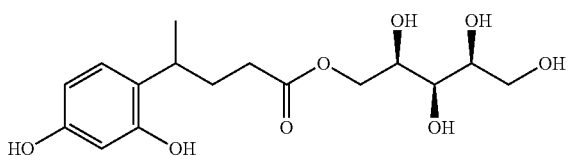

32

To a solution of compound 1 (1 g, 4.8 mmol) in 50 ml of acetonitrile were added benzyl bromide (5 eq) and potassium carbonate (5 eq). The mixture was refluxed for 20 h and, after filtration and removal of the solvent under vacuum, was subjected to silica gel chromatography (eluent: EtOAc/PE=1/2) to give a perbenzylated intermediate with a yield of 83% in the form of an oil (1.9 g). This intermediate was saponified with potassium hydroxide in aqueous methanol at 70° C. for 20 h, to give dibenzylated resorcinol carboxylic acid (after acid treatment), which was used in the next step. To 0.33 g of the latter (0.84 mmol) in 15 ml of DMF were added EDCI (0.242 g, 1.26 mmol), DMAP (0.4 g) and 2,3:4,5-di-O-isopropylidene-D-xylitol (0.588 g, 2.5 mmol) in sequence at 0° C. After stirring at ambient temperature for 20 h, the mixture was adjusted to pH=7 using 3N HCl. The solution was then poured into water and extracted twice with ethyl acetate. The combined extracts were washed with water and brine, dried over sodium sulfate and evaporated. The resulting residue was purified by silica gel chromatography (CH$_2$Cl$_2$/MeOH=50:1) to give 0.28 g (55%) of protected alcohol as oil. This oil was subjected to a deprotection of the acetonides and subsequent hydrogenolysis, to give compound 33 (yield 27% two steps) in the form of a hydroscopic oil.

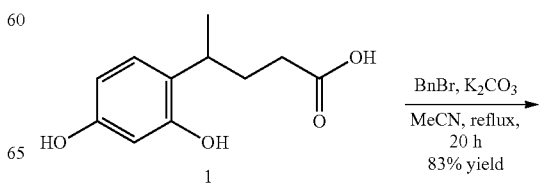

-continued

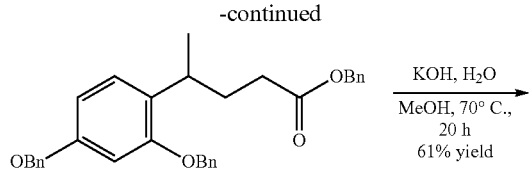

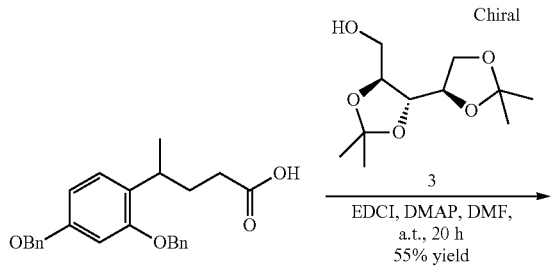

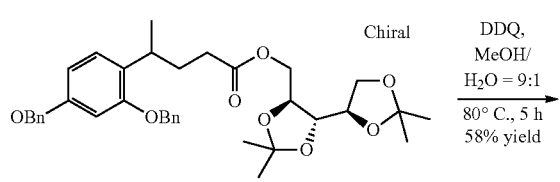

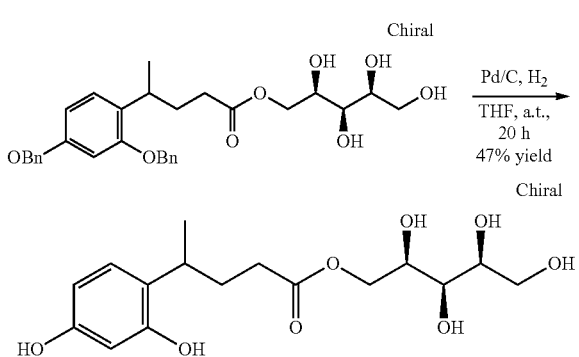

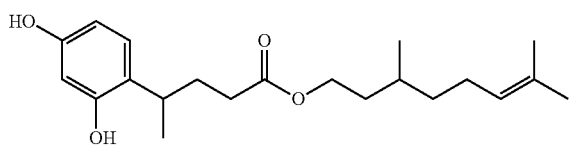

The MS and NMR spectra are in accordance with the desired product.

Example 33: Synthesis of Compound No. 33/3,7-dimethyloct-6-en-1-yl 4-(2,4-dihydroxyphenyl)pentanoate

33

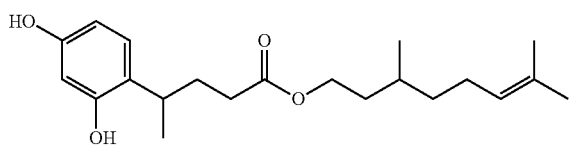

The same procedure as for compound 30 using (S) (−) citronellol at a.t. gives compound 33 in the form of an oil with a yield of 45%

The MS and NMR spectra are in accordance with the desired product.

Example 34: Synthesis of Compound No. 34/3-{[(2,2,5,5-tetramethyl-1,3-dioxan-4-yl)carbonyl]amino}propyl 4-(2,4-dihydroxyphenyl)pentanoate

34

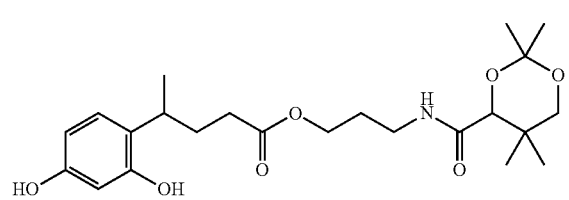

Panthenol acetonide (or (4R)—N-(3-hydroxypropyl)-2,2,5,5-tetramethyl-1,3-dioxane-4-carboxamide, commercially available) was condensed with benzylated carboxylic acid with EDCI and DMAP in dichloromethane to give 3.4 g of the benzylated intermediate. The hydrogenolysis was carried out, to give compound 34 in the form of a yellow oil.

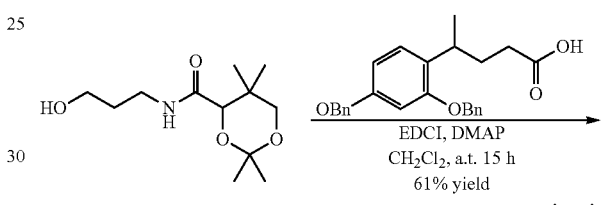

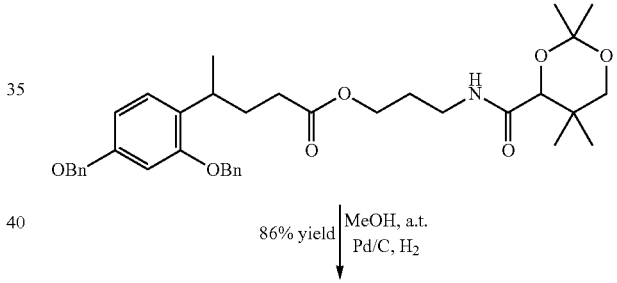

The MS and NMR spectra are in accordance with the desired product.

Example 35: Demonstration of the Depigmenting Activity

The effectiveness was demonstrated on the basis of the following test:

For the evaluations of the effect of prevention or of decrease of pigmentation of the skin and/or of lightening of this skin, the examples are carried out in the following way.

The measurement of the depigmenting activity (reduction of melanin production) of compounds of formula (I) was performed by assaying normal human melanocytes in vitro as follows.

First of all, normal human melanocytes were cultured and dispensed into 384 wells. After 24 hours, the culture medium was replaced with a medium containing compounds of formula (I) to be evaluated. The cells were incubated for 72 hours before measurement of the final optical density, which measures the amount of melanin produced by the melanocytes. A dose effect was performed using a wide concentration range of the compounds evaluated. Thus, by making the concentrations and the measurements of melanin correspond, it is possible to determine an IC50 in μM: concentration at which 50% decrease in melanin synthesis is achieved.

The compounds of formula (I) showed a strong depigmenting effect.

Various test campaigns were conducted and collated in the tables below.

TABLE 2

| Compound No. | IC50 (μM) | Maximum concentration tested (μM) |
| --- | --- | --- |
| 8 | 0.391 | 200 |
| 7 | 0.401 | 200 |
| 5 | 0.447 | 200 |
| 6 | 0.557 | 200 |
| 3 | 0.617 | 200 |
| 9 | 0.636 | 200 |
| 4 | 0.692 | 200 |
| 2 | 0.824 | 200 |
| 11 | 0.94 | 200 |
| 30 | 1.01 | 200 |
| 24 | 1.02 | 200 |
| 10 | 1.07 | 200 |
| 15 | 1.08 | 200 |
| 20 | 1.58 | 200 |
| 18 | 1.63 | 200 |
| 26 | 1.96 | 200 |
| 29 | 2.94 | 200 |
| 34 | 2.95 | 200 |
| 32 | 3.03 | 200 |
| 1 | 4.8 | 200 |

These results were compared with compounds described in the prior art, and more particularly in patent application WO 2004/017 936:

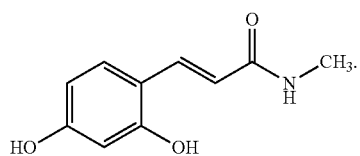

(A)

For this compound (A), the IC50 value is 3.86 μM.

in patent application WO 2005/085 169:

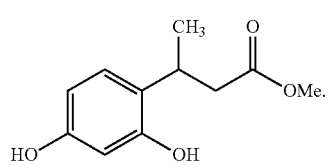

(B)

For this compound (B), the IC50 value is 4.97 μM.

in patent application EP623339/JP11255638:

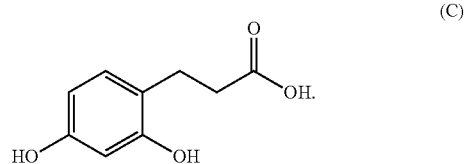 [SMILES: O=C(O)CCc1ccc(O)cc1O]

(C)

For this compound (C), the IC50 value is 63.1 μM.

TABLE 3

| Compound No. | IC50 (μM) | Maximum concentration tested (μM) |
| --- | --- | --- |
| 17 | 0.391 | 200 |
| 6 | 0.391 | 200 |
| 5 | 0.391 | 200 |
| 20 | 1.2 | 200 |
| 29 | 1.82 | 200 |
| 25 | 5.27 | 200 |
| 22 | 8.33 | 200 |
| 14 | 18.5 | 200 |
| 28 | 31.1 | 200 |
| 27 | 51.3 | 200 |

Example 36: Demonstration of the Depigmenting Activity

Two other tests were carried out:

The modulatory effect on melanogenesis of each compound was measured according to the method described in the patent FR-A-2734825, and also in the article by R. Schmidt, P. Krien and M. Régnier, Anal. Biochem., 235(2), 113-18, 1996. This test is carried out on a coculture of keratinocytes and melanocytes.

For the compounds tested, the following were determined:
the cytotoxicity,
the inhibitory activity on melanin synthesis, by estimating the melanin optical density,
the IC50 values (concentration for which 50% of the melanin synthesis is inhibited).

Compound 17: non-cytotoxic IC50=0.12 μM,

Compound 26: non-cytotoxic IC50=0.45 μM,

Compound 6: non-cytotoxic IC50=0.14 μM, 4-n-butyl resorcinol (reference) IC50=0.79 μM.

Example 37: Demonstration of the Depigmenting Activity

Experiment on pigmented reconstructed epidermis

| Compound | Effective concentration | Comparison of melanin with respect to the solvent (DMSO) |
| --- | --- | --- |
| Lucinol (4-n-butyl resorcinol) | 500 μM | −25% |
| Compound 2 | 50 μM | −26% |

Compound 2 has a depigmenting efficiency which is greater than lucinol on pigmented reconstructed epidermis.

Example 38: Cosmetic Composition

A skin depigmenting composition is prepared, comprising (in grams):

| | |
|---|---|
| Compound No. 2 | 2 g |
| PEG400 | 68 g |
| Ethanol | 30 g |

The composition applied to the skin makes it possible to attenuate brown spots.

Example 39: Gel

A skin depigmenting gel is prepared, comprising (% by weight):

| | |
|---|---|
| Compound No. 2 | 0.25% |
| Carbomer (Carbopol 981 from Lubrizol) | 1% |
| preserving agent | qs |
| water | qs 100% |

The composition applied to the skin makes it possible to attenuate brown spots.

The invention claimed is:

1. A compound chosen from:

| Compound No. | Structure | Chemical name |
|---|---|---|
| 2 | 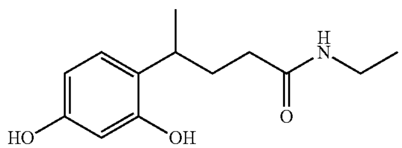 [SMILES: CCNC(=O)CCC(C)c1ccc(O)cc1O] | 4-(2,4-dihydroxyphenyl)-N-ethylpentanamide |
| 3 | 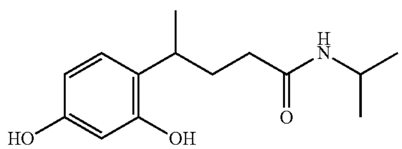 | 4-(2,4-dihydroxyphenyl)-N-(propan-2-yl)pentanamide |
| 4 | 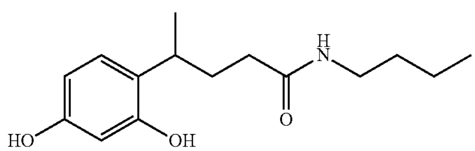 [SMILES: CCCCNC(=O)CCC(C)c1ccc(O)cc1O] | N-butyl-4-(2,4-dihydroxyphenyl)pentanamide |
| 5 | 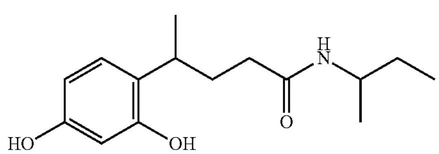 [SMILES: CCC(C)NC(=O)CCC(C)c1ccc(O)cc1O] | N-(butan-2-yl)-4-(2,4-dihydroxyphenyl)pentanamide |
| 6 | 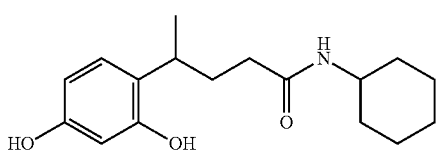 [SMILES: CC(CCC(=O)NC1CCCCC1)c1ccc(O)cc1O] | N-cyclohexyl-4-(2,4-dihydroxyphenyl)pentanamide |
| 7 | 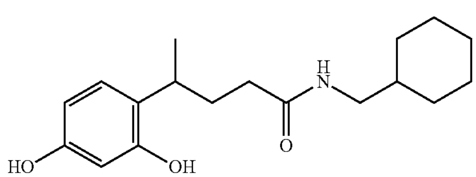 [SMILES: CC(CCC(=O)NCC1CCCCC1)c1ccc(O)cc1O] | N-(cyclohexylmethyl)-4-(2,4-dihydroxyphenyl)pentanamide |
| 8 | 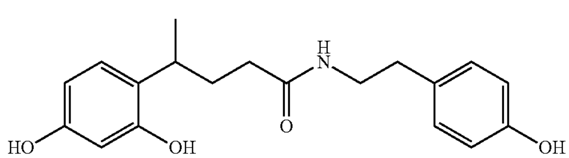 [SMILES: CC(CCC(=O)NCCc1ccc(O)cc1)c1ccc(O)cc1O] | 4-(2,4-dihydroxyphenyl)-N-[2-(4-hydroxyphenyl)ethyl]pentanamide |

-continued

| Compound No. | Structure | Chemical name |
|---|---|---|
| 9 | 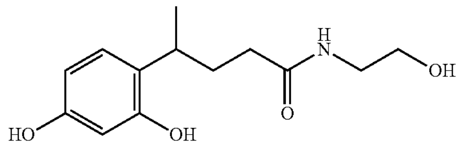 [SMILES: CC(CCC(=O)NCCO)c1ccc(O)cc1O] | 4-(2,4-dihydroxyphenyl)-N-(2-hydroxyethyl)pentanamide |
| 10 | 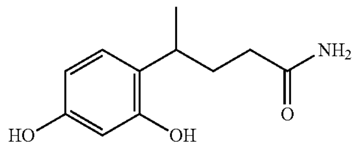 | 4-(2,4-dihydroxyphenyl)pentanamide |
| 11 | 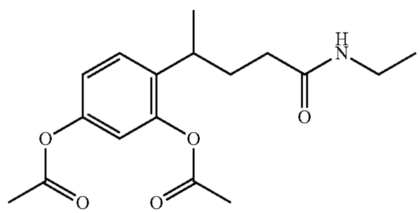 [SMILES: CCNC(=O)CCC(C)c1ccc(OC(C)=O)cc1OC(C)=O] | 4-[5-(ethylamino)-5-oxopentan-2-yl]benzene-1,3-diyl diacetate |
| 12 | 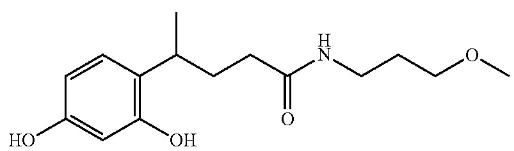 [SMILES: COCCCNC(=O)CCC(C)c1ccc(O)cc1O] | 4-(2,4-dihydroxyphenyl)-N-(3-methoxypropyl)pentanamide |
| 13 | 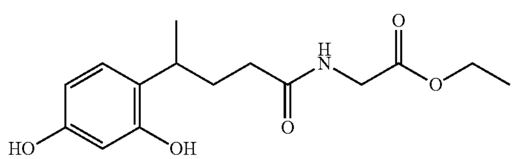 [SMILES: CCOC(=O)CNC(=O)CCC(C)c1ccc(O)cc1O] | ethyl N-[4-(2,4-dihydroxyphenyl)pentanoyl]glycinate |
| 14 | 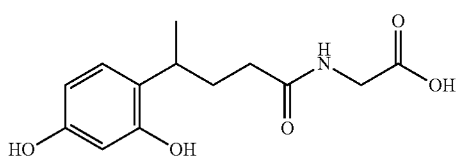 [SMILES: CC(CCC(=O)NCC(=O)O)c1ccc(O)cc1O] | N-[4-(2,4-dihydroxyphenyl)pentanoyl]glycine |
| 15 | 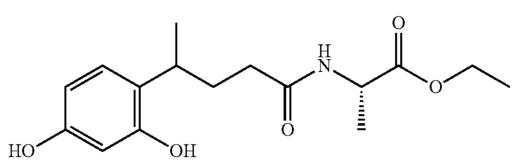 [SMILES: CCOC(=O)[C@H](C)NC(=O)CCC(C)c1ccc(O)cc1O] | ethyl N-[4-(2,4-dihydroxyphenyl)pentanoyl]-L-alaninate |
| 16 | 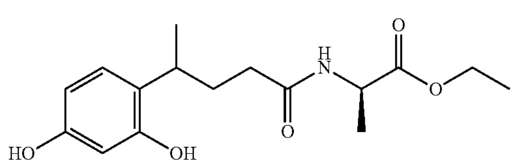 [SMILES: CCOC(=O)[C@@H](C)NC(=O)CCC(C)c1ccc(O)cc1O] | ethyl N-[4-(2,4-dihydroxyphenyl)pentanoyl]-D-alaninate |
| 17 | 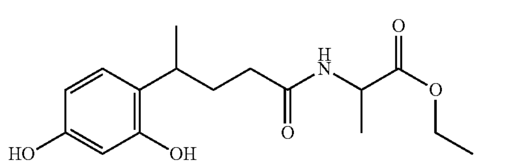 [SMILES: CCOC(=O)C(C)NC(=O)CCC(C)c1ccc(O)cc1O] | Ethyl N-[4-(2,4-dihydroxyphenyl)pentanoyl] DL alaninate |

-continued

| Compound No. | Structure | Chemical name |
|---|---|---|
| 18 | 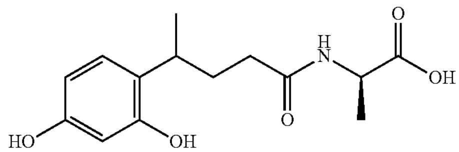 [SMILES: CC(CCC(=O)N[C@H](C)C(=O)O)c1ccc(O)cc1O] | N-[4-(2,4-dihydroxyphenyl)pentanoyl]-D-alanine |
| 19 | 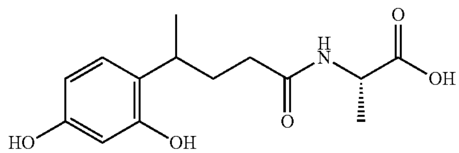 [SMILES: CC(CCC(=O)N[C@@H](C)C(=O)O)c1ccc(O)cc1O] | N-[4-(2,4-dihydroxyphenyl)pentanoyl]-L-alanine |
| 20 | 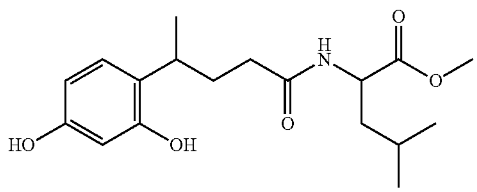 [SMILES: COC(=O)C(CC(C)C)NC(=O)CCC(C)c1ccc(O)cc1O] | methyl N-[4-(2,4-dihydroxyphenyl)pentanoyl]leucinate |
| 21 | 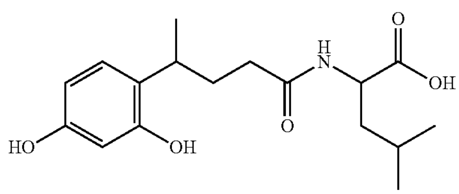 [SMILES: CC(C)CC(NC(=O)CCC(C)c1ccc(O)cc1O)C(=O)O] | N-[4-(2,4-dihydroxyphenyl)pentanoyl]leucine |
| 22 | 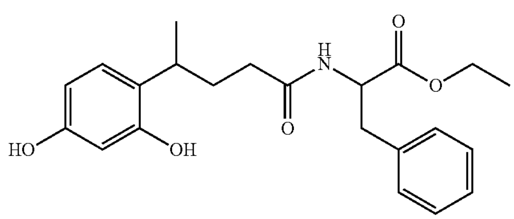 [SMILES: CCOC(=O)C(Cc1ccccc1)NC(=O)CCC(C)c1ccc(O)cc1O] | ethyl N-[4-(2,4-dihydroxyphenyl)pentanoyl]phenylalaninate |
| 23 | 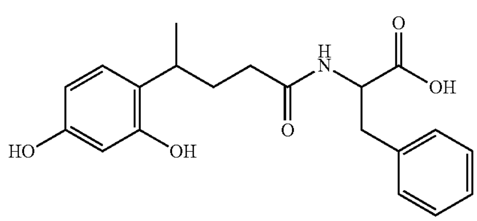 [SMILES: CC(CCC(=O)NC(Cc1ccccc1)C(=O)O)c1ccc(O)cc1O] | N-[4-(2,4-dihydroxyphenyl)pentanoyl]phenylalanine |
| 24 | 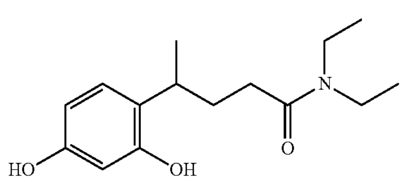 [SMILES: CCN(CC)C(=O)CCC(C)c1ccc(O)cc1O] | 4-(2,4-dihydroxyphenyl)-N,N-diethylpentanamide |
| 25 | 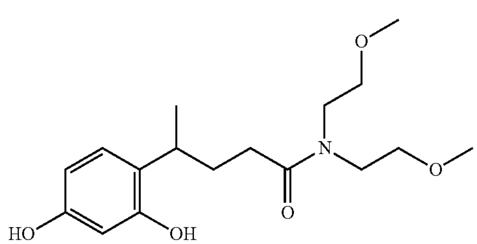 [SMILES: COCCN(CCOC)C(=O)CCC(C)c1ccc(O)cc1O] | 4-(2,4-dihydroxyphenyl)-N,N-bis(2-methoxyethyl)pentanamide |

-continued

| Compound No. | Structure | Chemical name |
|---|---|---|
| 26 | 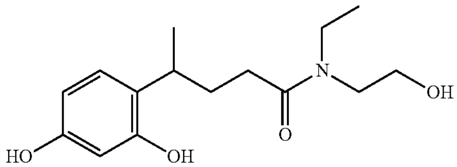 [SMILES: CCN(CCO)C(=O)CCC(C)c1ccc(O)cc1O] | 4-(2,4-dihydroxyphenyl)-N-ethyl-N-(2-hydroxyethyl)pentanamide |
| 27 | 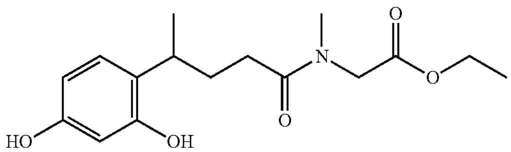 [SMILES: CCOC(=O)CN(C)C(=O)CCC(C)c1ccc(O)cc1O] | ethyl N-[4-(2,4-dihydroxyphenyl)pentanoyl]-N-methylglycinate |
| 28 | 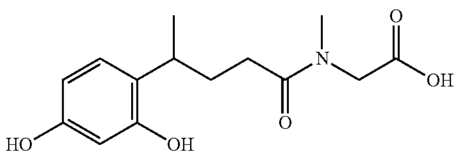 | N-[4-(2,4-dihydroxyphenyl)pentanoyl]-N-methylglycine |
| 29 | 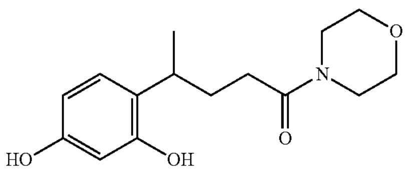 [SMILES: CC(CCC(=O)N1CCOCC1)c1ccc(O)cc1O] | 4-(2,4-dihydroxyphenyl)-1-(morpholin-4-yl)pentan-1-one |
| 30 | 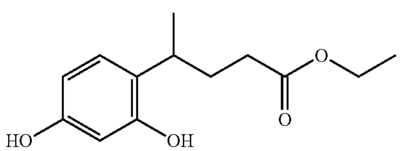 [SMILES: CCOC(=O)CCC(C)c1ccc(O)cc1O] | ethyl 4-(2,4-dihydroxyphenyl)pentanoate |
| 31 | 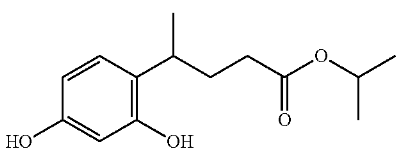 [SMILES: CC(C)OC(=O)CCC(C)c1ccc(O)cc1O] | propan-2-yl 4-(2,4-dihydroxyphenyl)pentanoate |
| 32 | 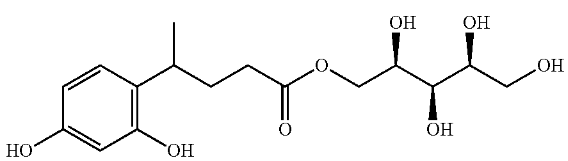 [SMILES: CC(CCC(=O)OC[C@@H](O)[C@H](O)[C@@H](O)CO)c1ccc(O)cc1O] | 5-O-[4-(2,4-dihydroxyphenyl)pentanoyl]-D-xylitol |
| 33 | 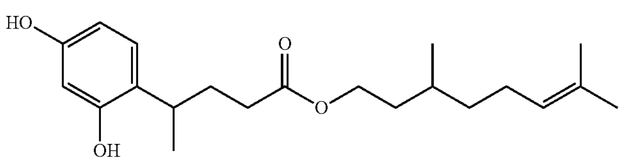 [SMILES: CC(C)=CCCC(C)CCOC(=O)CCC(C)c1ccc(O)cc1O] | 3,7-dimethyloct-6-en-1-yl 4-(2,4-dihydroxyphenyl)pentanoate |
| 34 | 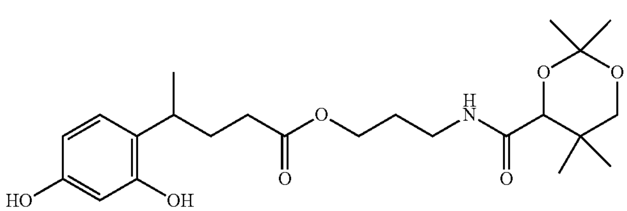 [SMILES: CC(CCC(=O)OCCCNC(=O)C1OC(C)(C)OCC1(C)C)c1ccc(O)cc1O] | 3-{[(2,2,5,5-tetramethyl-1,3-dioxan-4-yl)carbonyl]amino}propyl 4-(2,4-dihydroxyphenyl)pentanoate, |

, the non-toxic salts thereof, solvates thereof, optical and/or geometrical isomers thereof, racemic mixtures thereof, alone or mixtures thereof.

2. The compound according to claim 1, chosen from:

| Compound No. | Structure | Chemical name |
|---|---|---|
| 2 | 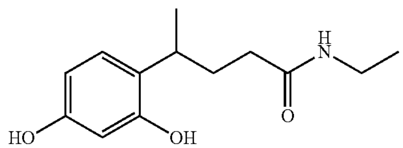 [SMILES: CCNC(=O)CCC(C)c1ccc(O)cc1O] | 4-(2,4-dihydroxyphenyl)-N-ethylpentanamide |
| 3 | 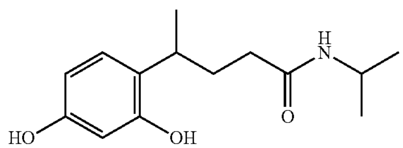 [SMILES: CC(C)NC(=O)CCC(C)c1ccc(O)cc1O] | 4-(2,4-dihydroxyphenyl)-N-(propan-2-yl)pentanamide |
| 4 | 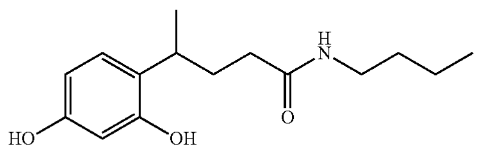 [SMILES: CCCCNC(=O)CCC(C)c1ccc(O)cc1O] | N-butyl-4-(2,4-dihydroxyphenyl)pentanamide |
| 5 | 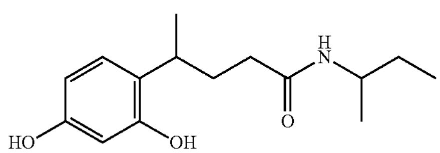 [SMILES: CCC(C)NC(=O)CCC(C)c1ccc(O)cc1O] | N-(butan-2-yl)-4-(2,4-dihydroxyphenyl)pentanamide |
| 6 | 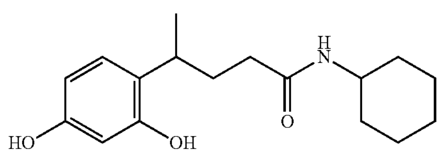 [SMILES: CC(CCC(=O)NC1CCCCC1)c1ccc(O)cc1O] | N-cyclohexyl-4-(2,4-dihydroxyphenyl)pentanamide |
| 7 | 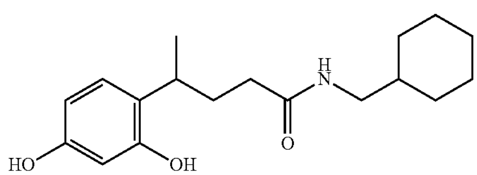 [SMILES: CC(CCC(=O)NCC1CCCCC1)c1ccc(O)cc1O] | N-(cyclohexylmethyl)-4-(2,4-dihydroxyphenyl)pentanamide |
| 8 | 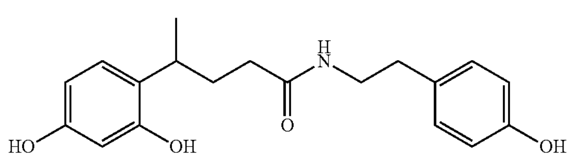 [SMILES: CC(CCC(=O)NCCc1ccc(O)cc1)c1ccc(O)cc1O] | 4-(2,4-dihydroxyphenyl)-N-[2-(4-hydroxyphenyl)ethyl]pentanamide |
| 9 | 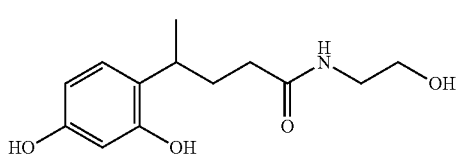 [SMILES: CC(CCC(=O)NCCO)c1ccc(O)cc1O] | 4-(2,4-dihydroxyphenyl)-N-(2-hydroxyethyl)pentanamide |
| 10 | 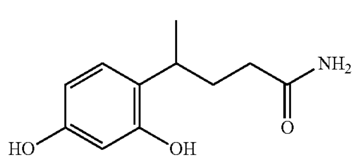 | 4-(2,4-dihydroxyphenyl)pentanamide |

-continued

| Compound No. | Structure | Chemical name |
|---|---|---|
| 11 | 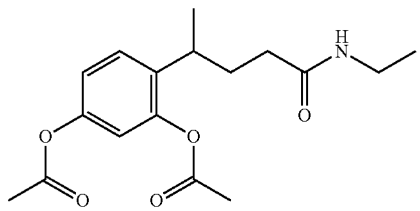 [SMILES: CCNC(=O)CCC(C)c1ccc(OC(C)=O)cc1OC(C)=O] | 4-[5-(ethylamino)-5-oxopentan-2-yl]benzene-1,3-diyl diacetate |
| 14 | 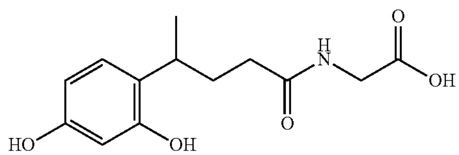 | N-[4-(2,4-dihydroxyphenyl)pentanoyl]glycine |
| 15 | 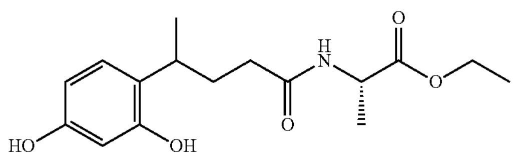 [SMILES: CCOC(=O)[C@H](C)NC(=O)CCC(C)c1ccc(O)cc1O] | ethyl N-[4-(2,4-dihydroxyphenyl)pentanoyl]-L-alaninate |
| 17 | 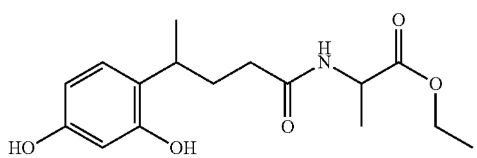 [SMILES: CCOC(=O)C(C)NC(=O)CCC(C)c1ccc(O)cc1O] | Ethyl N-[4-(2,4-dihydroxyphenyl)pentanoyl] DL alaninate |
| 18 | 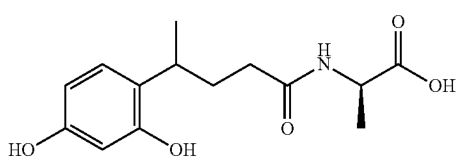 [SMILES: CC(CCC(=O)N[C@H](C)C(=O)O)c1ccc(O)cc1O] | N-[4-(2,4-dihydroxyphenyl)pentanoyl]-D-alanine |
| 20 | 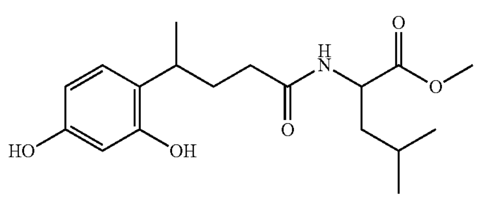 [SMILES: COC(=O)C(CC(C)C)NC(=O)CCC(C)c1ccc(O)cc1O] | methyl N-[4-(2,4-dihydroxyphenyl)pentanoyl]leucinate |
| 22 | 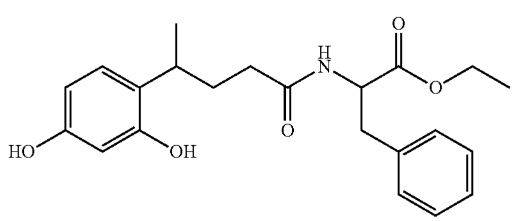 [SMILES: CCOC(=O)C(Cc1ccccc1)NC(=O)CCC(C)c1ccc(O)cc1O] | ethyl N-[4-(2,4-dihydroxyphenyl)pentanoyl]phenylalaninate |
| 24 | 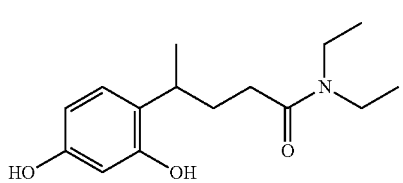 [SMILES: CCN(CC)C(=O)CCC(C)c1ccc(O)cc1O] | 4-(2,4-dihydroxyphenyl)-N,N-diethylpentanamide |

-continued

| Compound No. | Structure | Chemical name |
|---|---|---|
| 25 | 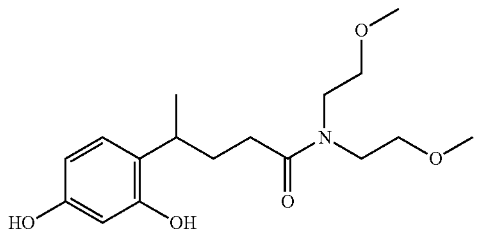 [SMILES: COCCN(CCOC)C(=O)CCC(C)c1ccc(O)cc1O] | 4-(2,4-dihydroxyphenyl)-N,N-bis(2-methoxyethyl)pentanamide |
| 26 | 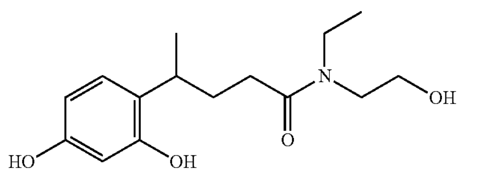 [SMILES: CCN(CCO)C(=O)CCC(C)c1ccc(O)cc1O] | 4-(2,4-dihydroxyphenyl)-N-ethyl-N-(2-hydroxyethyl)pentanamide |
| 27 | 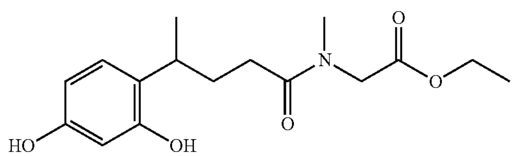 [SMILES: CCOC(=O)CN(C)C(=O)CCC(C)c1ccc(O)cc1O] | ethyl N-[4-(2,4-dihydroxyphenyl)pentanoyl]-N-methylglycinate |
| 28 | 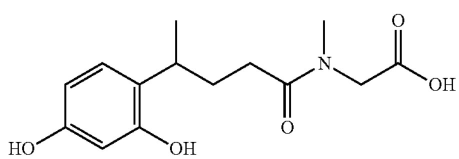 [SMILES: CC(CCC(=O)N(C)CC(=O)O)c1ccc(O)cc1O] | N-[4-(2,4-dihydroxyphenyl)pentanoyl]-N-methylglycine |
| 29 | 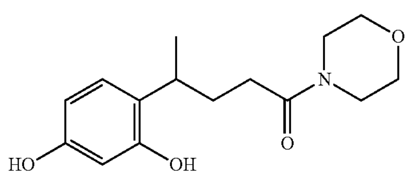 [SMILES: CC(CCC(=O)N1CCOCC1)c1ccc(O)cc1O] | 4-(2,4-dihydroxyphenyl)-1-(morpholin-4-yl)pentan-1-one |
| 30 | 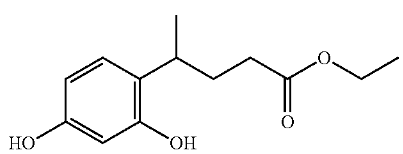 [SMILES: CCOC(=O)CCC(C)c1ccc(O)cc1O] | ethyl 4-(2,4-dihydroxyphenyl)pentanoate |
| 32 | 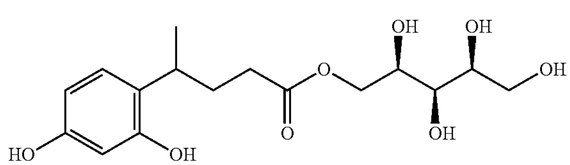 [SMILES: CC(CCC(=O)OC[C@@H](O)[C@H](O)[C@@H](O)CO)c1ccc(O)cc1O] | 5-O-[4-(2,4-dihydroxyphenyl)pentanoyl]-D-xylitol |
| 34 | 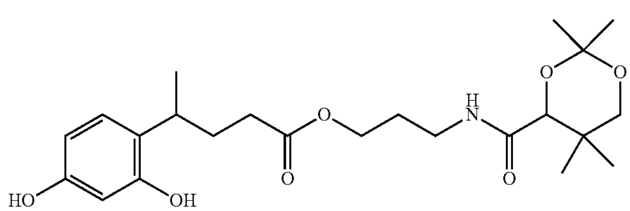 [SMILES: CC(CCC(=O)OCCCNC(=O)C1OC(C)(C)OCC1(C)C)c1ccc(O)cc1O] | 3-{[(2,2,5,5-tetramethyl-1,3-dioxan-4-yl)carbonyl]amino}propyl 4-(2,4-dihydroxyphenyl)pentanoate. |

, the non-toxic salts thereof, solvates thereof, optical and/or geometrical isomers thereof, racemic mixtures thereof, alone or mixtures thereof.

3. A cosmetic composition comprising, in a physiologically acceptable medium, a compound according to claim 1.

4. The composition according to claim 3, wherein the compound (I) is present in a content of between 0.01% and 10% by weight relative to the total weight of the composition.

5. The composition according to claim 3, which comprises at least one adjuvant chosen from the group of organic solvents; waxes, pigments, fillers, dyes, surfactants, emulsifiers; cosmetic active agents, organic or inorganic photoprotective agents, polymers, thickeners, preserving agents, fragrances, bactericides, ceramides, odour absorbers, and antioxidants.

6. The composition according to claim 3, which comprises at least one active agent chosen from: desquamating agents; calmatives, organic or inorganic photo protective agents, moisturizers; depigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; tensioning agents; anti-pollution agents and/or free-radical scavengers; agents acting on the capillary circulation; agents acting on the energy metabolism of cells; and mixtures thereof.

7. The compound according to claim 1, chosen from 4-(2,4-dihydroxyphenyl)-N-ethylpentanamide, represented by the formula:

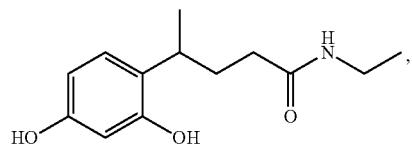 [SMILES: CCNC(=O)CCC(C)c1ccc(O)cc1O]

the non-toxic salts thereof, solvates thereof, optical and/or geometrical isomers thereof, racemic mixtures thereof, alone or mixtures thereof.

8. The compound according to claim 1, chosen from 4-(2,4-dihydroxyphenyl)-N-[2-(4-hydroxyphenyl)ethyl] pentanamide, represented by the formula:

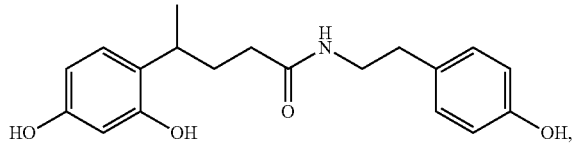 [SMILES: CC(CCC(=O)NCCc1ccc(O)cc1)c1ccc(O)cc1O]

the non-toxic salts thereof, solvates thereof, optical and/or geometrical isomers thereof, racemic mixtures thereof, alone or mixtures thereof.

* * * * *